US009687668B2

(12) United States Patent
McKenna et al.

(10) Patent No.: US 9,687,668 B2
(45) Date of Patent: Jun. 27, 2017

(54) TREATMENT OF CANCER IN BODY CAVITIES AND PARTS THAT ARE CAVITY-LIKE

(75) Inventors: Daniel B. McKenna, Vail, CO (US); Robert J. Tondu, Houston, TX (US); Alireza Mashal, Middleton, WI (US); Karl M. Frantz, Broomfield, CO (US); Martin A. Huisjen, Boulder, CO (US)

(73) Assignee: ENDOMAGNETICS LIMITED, Cambridge (GB)

( * ) Notice: Subject to any disclaimer, the term of this patent is extended or adjusted under 35 U.S.C. 154(b) by 31 days.

(21) Appl. No.: 13/590,515

(22) Filed: Aug. 21, 2012

(65) Prior Publication Data
US 2013/0053619 A1   Feb. 28, 2013

Related U.S. Application Data

(60) Provisional application No. 61/527,928, filed on Aug. 26, 2011, provisional application No. 61/527,973, filed on Aug. 26, 2011.

(51) Int. Cl.
*A61M 37/00* (2006.01)
*A61N 2/00* (2006.01)
(Continued)

(52) U.S. Cl.
CPC ............. *A61N 2/002* (2013.01); *A61M 25/10* (2013.01); *A61M 37/00* (2013.01); *A61N 1/406* (2013.01);
(Continued)

(58) Field of Classification Search
CPC .......... A61K 2035/124; A61K 41/0052; A61K 49/1863; A61K 49/1896; B82Y 5/00; C12N 5/0663; C12N 2529/00; A61N 5/10
(Continued)

(56) References Cited

U.S. PATENT DOCUMENTS

| 4,346,715 A | 8/1982 | Gammell |
| 5,099,756 A | 3/1992 | Franconi et al. |

(Continued)

FOREIGN PATENT DOCUMENTS

| CN | 1694657 | 11/2005 |
| CN | 101854977 | 10/2010 |

(Continued)

OTHER PUBLICATIONS

Machine Translation in English of JP07213507, Aug. 15, 1995 (attached).*

(Continued)

*Primary Examiner* — Navin Natnithithadha
*Assistant Examiner* — Sunita Reddy
(74) *Attorney, Agent, or Firm* — K&L Gates LLP

(57) ABSTRACT

The Body Cavity Cancer Treatment System achieves extremely uniform temperatures inside the tissue of the body cavity thereby realizing optimal efficacy in enhancing operation of the chemotherapy agent while avoiding harm or pain to the patient. This is accomplished by the inclusion of "target particles", such as nano-particles, into the body cavity along with the chemotherapy agent to enable the use of an externally generated energy field to cause heating of the chemotherapy agent and the surrounding tissue of the body cavity by the activation of the nano-particles. The proper selection of the applied energy field enables precise control of the heat generated by the movement of the nano-particles.

13 Claims, 19 Drawing Sheets

(51) Int. Cl.
*A61N 1/40* (2006.01)
*A61M 25/10* (2013.01)
*A61N 2/02* (2006.01)
*A61N 5/10* (2006.01)

(52) U.S. Cl.
CPC .............. *A61N 2/004* (2013.01); *A61N 2/02* (2013.01); *A61M 2025/105* (2013.01); *A61M 2037/0007* (2013.01); *A61M 2205/3368* (2013.01); *A61N 5/10* (2013.01)

(58) Field of Classification Search
USPC ........ 600/9, 10, 12, 13, 2; 242/9.3; 977/773, 977/906
See application file for complete search history.

(56) References Cited

U.S. PATENT DOCUMENTS

| | | | |
|---|---|---|---|
| 5,621,188 | A | 4/1997 | Lee et al. |
| 6,149,576 | A | 11/2000 | Gray et al. |
| 6,165,440 | A | 12/2000 | Esenaliev |
| 6,238,421 | B1 | 5/2001 | Gunther et al. |
| 6,423,056 | B1 | 7/2002 | Ishikawa et al. |
| 6,530,944 | B2 | 3/2003 | West et al. |
| 6,961,620 | B2 | 11/2005 | Rioux et al. |
| 6,997,863 | B2 | 2/2006 | Handy et al. |
| 7,133,725 | B2 | 11/2006 | Stirbl et al. |
| 7,174,217 | B2 | 2/2007 | Rioux et al. |
| 7,623,908 | B2 | 11/2009 | Boppart et al. |
| 7,691,285 | B2 | 4/2010 | Teller et al. |
| 7,819,835 | B2 | 10/2010 | Landy et al. |
| 7,842,281 | B2 | 11/2010 | Haik et al. |
| 7,951,061 | B2 | 5/2011 | Foreman et al. |
| 2001/0012912 | A1 | 8/2001 | Feucht |
| 2002/0091377 | A1 | 7/2002 | Anderson et al. |
| 2002/0193784 | A1 | 12/2002 | McHale et al. |
| 2003/0032995 | A1 | 2/2003 | Handy et al. |
| 2004/0236278 | A1 | 11/2004 | Herweck et al. |
| 2005/0015049 | A1 | 1/2005 | Rioux et al. |
| 2005/0059852 | A1 | 3/2005 | Rioux et al. |
| 2005/0090732 | A1 | 4/2005 | Ivkov et al. |
| 2005/0171433 | A1 | 8/2005 | Boppart et al. |
| 2005/0215988 | A1 | 9/2005 | Altshuler et al. |
| 2005/0249817 | A1 | 11/2005 | Haik et al. |
| 2005/0271745 | A1 | 12/2005 | Gruettner et al. |
| 2006/0015098 | A1 | 1/2006 | Rioux et al. |
| 2006/0142748 | A1 | 6/2006 | Foreman et al. |
| 2006/0163526 | A1 | 7/2006 | Teller et al. |
| 2006/0269612 | A1 | 11/2006 | Xiang et al. |
| 2007/0010702 | A1 | 1/2007 | Wang et al. |
| 2007/0135373 | A1 | 6/2007 | Li et al. |
| 2007/0258889 | A1 | 11/2007 | Douglas et al. |
| 2008/0103355 | A1 | 5/2008 | Boyden et al. |
| 2008/0114429 | A1 | 5/2008 | Nagano et al. |
| 2008/0300571 | A1 | 12/2008 | LePivert |
| 2008/0319375 | A1 | 12/2008 | Hardy |
| 2009/0043256 | A1 | 2/2009 | Landy et al. |
| 2009/0054722 | A1 | 2/2009 | Sugano et al. |
| 2009/0076496 | A1 | 3/2009 | Azure |
| 2009/0076502 | A1 | 3/2009 | Azure et al. |
| 2009/0157069 | A1 | 6/2009 | Tom et al. |
| 2009/0220968 | A1 | 9/2009 | Issadore et al. |
| 2009/0287036 | A1 | 11/2009 | Shapiro et al. |
| 2010/0016783 | A1 | 1/2010 | Bourke, Jr. et al. |
| 2010/0052668 | A1 | 3/2010 | Gleich et al. |
| 2010/0056643 | A1 | 3/2010 | Bachynsky et al. |
| 2010/0099941 | A1 | 4/2010 | Haik et al. |
| 2010/0160483 | A1 | 6/2010 | Vogt et al. |
| 2010/0204674 | A1* | 8/2010 | Forbes et al. ................. 604/500 |
| 2010/0222774 | A1 | 9/2010 | Hegg et al. |
| 2010/0292564 | A1 | 11/2010 | Cantillon Murphy |
| 2010/0310636 | A1* | 12/2010 | Sharma et al. ............... 424/450 |
| 2011/0104305 | A1 | 5/2011 | Day et al. |
| 2011/0125232 | A1 | 5/2011 | Landy et al. |
| 2011/0137230 | A1 | 6/2011 | Altshuler et al. |
| 2011/0177153 | A1 | 7/2011 | Zhu |
| 2012/0065492 | A1* | 3/2012 | Gertner .................. A61B 5/055 600/411 |
| 2012/0203050 | A1* | 8/2012 | Levy et al. ...................... 600/1 |
| 2012/0259154 | A1 | 10/2012 | Hong et al. |
| 2013/0053619 | A1 | 2/2013 | McKenna et al. |
| 2013/0053620 | A1 | 2/2013 | Susedik et al. |
| 2013/0211249 | A1* | 8/2013 | Barnett ................ A61K 9/0019 600/435 |

FOREIGN PATENT DOCUMENTS

| | | |
|---|---|---|
| CN | 102008782 | 4/2011 |
| JP | 04-276263 A | 10/1992 |
| JP | 04-348765 A | 12/1992 |
| JP | 05-245217 A | 9/1993 |
| JP | 2005-523736 A | 8/2005 |
| JP | 2007500060 A | 1/2007 |
| JP | 2007521109 A | 8/2007 |
| JP | 2010-512910 A | 4/2010 |
| JP | 2011-032238 A | 2/2011 |
| WO | 03/022360 A3 | 3/2003 |
| WO | 2004033038 A2 | 4/2004 |
| WO | 2004105833 A2 | 12/2004 |
| WO | 2005044365 A2 | 5/2005 |
| WO | WO-2010139386 A1 | 12/2010 |

OTHER PUBLICATIONS

Barnes et al.; *Bioengineering and Biophysical Aspects of Electromagnetic Fields*, Third Edition, 2007; p. 298 and 299.
International Search Report in corresponding PCT Application No. PCT/US11/68114 dated Apr. 19, 2012, 3 pages.
International Search Report in corresponding PCT Application No. PCT/US11/68116 dated May 8, 2012, 3 pages.
International Search Report in corresponding PCT Application No. PCT/US11/68134 dated May 8, 2012, 3 pages.
International Search Report in corresponding PCT Application No. PCT/US11/68142 dated May 4, 2012, 3 pages.
International Search Report in corresponding PCT Application No. PCT/US11/68146 dated May 2, 2012, 3 pages.
International Search Report in corresponding PCT Application No. PCT/US11/68154 dated May 3, 2012, 3 pages.
In the US Patent and Trademark Office U.S. Appl. No. 13/012,527 Non-Final Office Action dated Apr. 29, 2013, 13 pages.
In the US Patent and Trademark Office U.S. Appl. No. 13/012,560 Non-Final Office Action dated Apr. 25, 2013, 9 pages.
In the US Patent and Trademark Office U.S. Appl. No. 13/012,572 Non-Final Office Action dated May 23, 2013, 12 pages.
International Search Report in corresponding PCT Application No. PCT/US12/51763 dated Oct. 22, 2012, 3 pages.
International Search Report in corresponding PCT Application No. PCT/US12/51765 dated Oct. 22, 2012, 3 pages.
Vertegel et al.; "Silica Nanoparticle Size Influences the Structure and Enzymatic Activity of Adsorbed Lysozyme," *Langmuir*, 2004; 20:6800-6807.
Wikipedia Physics of magnetic resonance imaging (2014), retrieved on Aug. 5, 2014 from http://en.wikipedia.org/wiki/Physics_of_magnetic_resonance_imaging.
Giustini, et al. "Magnetic Nanoparticle Hyperthermia in Cancer Treatment" Nano Life, Mar. 2010.
Sophie Laurenta et al. "Magnetic Fluid Hyperthermia: Focus on superparamagnetic iron oxide nanoparticles" Advances in Colloid and Interface Science, vol. 155, Issues 1-2, Aug. 10, 2011.

* cited by examiner

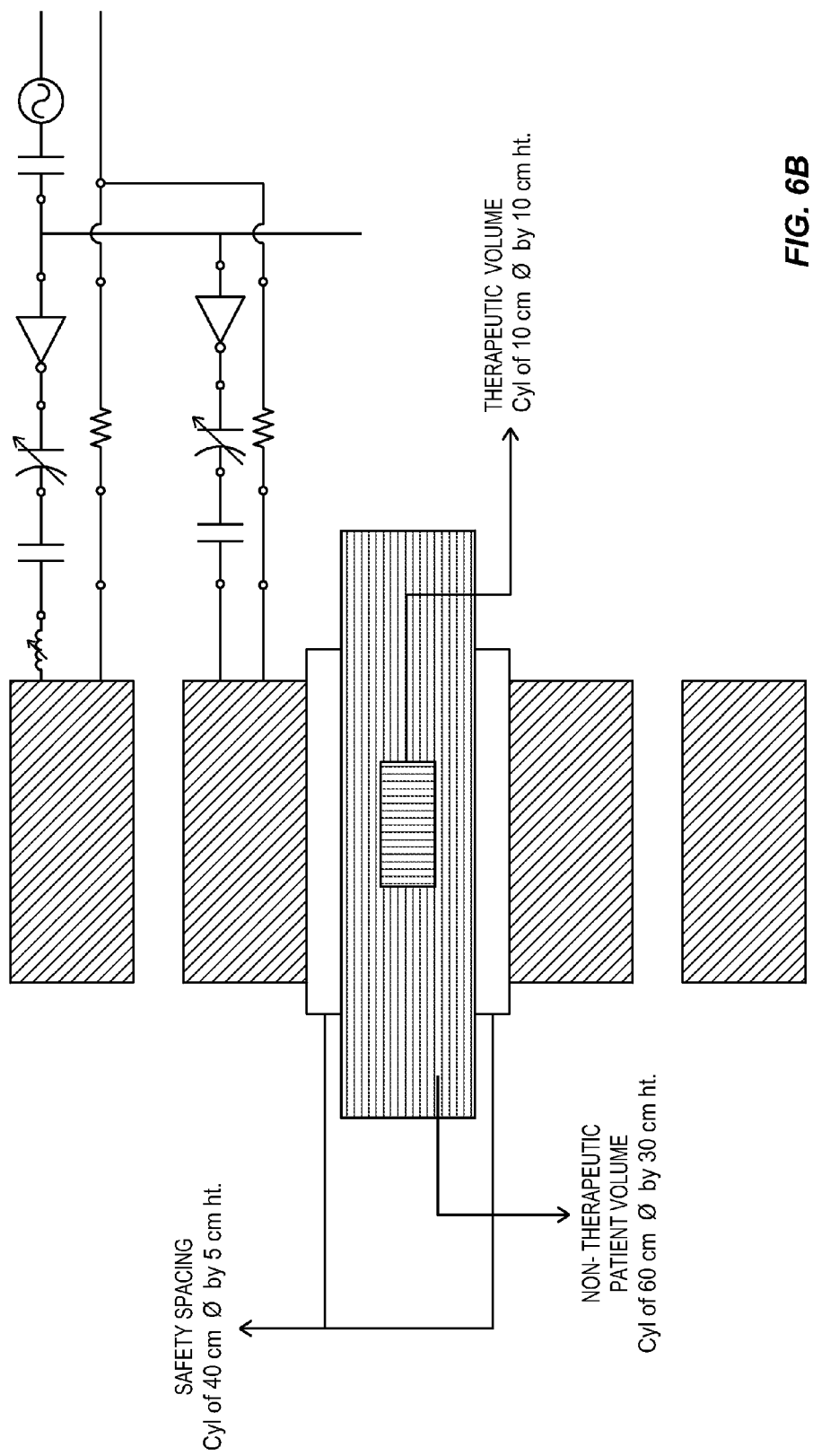

TREATMENT OF CANCER IN BODY CAVITIES AND PARTS THAT ARE CAVITY-LIKE

CROSS-REFERENCE TO RELATED APPLICATIONS

This application is related to an application filed on the same date hereof titled "Apparatus For The Generation Of An Energy Field For The Treatment of Cancer in Body Cavities And Parts That Are Cavity-Like", and also claims the benefit of U.S. Provisional Patent Application Ser. No. 61/527,928 filed on Aug. 26, 2011, titled "Treatment of Cancer in Body Cavities And Parts That Are Cavity-Like" and U.S. Provisional Patent Application Ser. No. 61/527,973 filed on Aug. 26, 2011, titled "Apparatus For The Generation Of An Energy Field For The Treatment of Cancer in Body Cavities And Parts That Are Cavity-Like."

FIELD OF THE INVENTION

The invention relates generally to the field of treatment of invasive agents, such as pathogens and cancers, in living organisms such as the human body and, more particularly, to a system that applies an energy field to the living organism, to activate particles which are infused into the living organism.

BACKGROUND OF THE INVENTION

Any time low temperature heat is added to a living organism, such as the human body, as it is being treated for cancer with radiation and/or chemotherapy, the efficacy of the cancer treatment is substantially increased. The difficulty with this process has been in "adding heat" to only the cancerous region that is being treated, in a precisely controlled manner.

One prior cancer treatment method sought to place the entire living organism in a hot water wrap which often caused severe side effects, including death, since the control of the patient's body temperature is not precise. This cancer treatment method often caused conditions similar to heat shock or heat stroke, since the living organism is unable to adequately remove the applied heat to maintain a safe body temperature.

Another cancer treatment approach, called regional hyperthermia, uses microwave energy, applied to the living organism from an external source, to heat the tissue. This approach relies on the fact that tissue is largely composed of water, which is dipolar in nature and heats as the water molecules "physically flip" in concert with the applied alternating current magnetic field. This "flip" causes molecular friction, hence heat. However, the microwave heating of tissue causes hot spots and burns (as do microwave ovens). In addition, it is virtually impossible to direct the microwave energy to only heat the tissue of interest; and surrounding non-cancerous tissue is therefore also heated, sometimes to a burning level. Studies have shown patients can receive $2^{nd}$ degree and $3^{rd}$ degree burns from a microwave heating approach.

A third cancer treatment approach uses an "antenna", such as a monopole, which is inserted via a catheter inside the body cavity to be heated. Again, as before, severe hot spots and burns can result from the non-uniform application of electromagnetic fields (at microwave frequencies) which has unintended damaging effects.

All of the cancer treatment methods embodied in the present prior art have significant deficiencies in terms of patient safety, treatment efficacy and cost. In addition, in the United States, the only approved procedure for the treatment of bladder cancer in humans is a pure chemotherapy based approach, without any heating of the bladder tissue or the chemotherapy medicine, to stress and help kill remaining cancer cells. Other approaches such as using microwave heating applied to the body from a source located outside the body are only in experimental, pre-clinical studies. The catheter based approach is only approved for use in certain European countries.

Thus, the present set of bladder cancer treatment methods can be characterized as:
- Chemotherapy without hyperthermia—minimal effectiveness.
- Radiation without hyperthermia—minimal effectiveness.
- Chemotherapy with microwave heating of bladder tissue causes burns, non-uniform heating, hot spots, cold spots, patient pain, patient discomfort, and inadvertently heats non-bladder tissue.
- Chemotherapy with catheter based radio frequency heating inside the bladder space via a small antenna causes burns, non-uniform heating, hot spots, cold spots, patient pain and patient discomfort.
- Circulating chemotherapy fluids won't work because of the physical size of the urethra, non-uniform thermodynamics (can't only remove "cold" fluid and replace it with "warm" fluid), re-circulating chemotherapy agents thru the urethra is caustic and very damaging, the urethra can be easily damaged by large physical objects inserted into it and last, the chemotherapy agent (such as Mitomycin C) is very expensive. All of this increases the volume of Mitomycin C required to ensure that the chemotherapy agent concentration is uniform in the total circulated volume of fluid (upwards of 4 to 5 times the nominal amount of Mitomycin C is necessary if circulated fluids is used).

BRIEF SUMMARY OF THE INVENTION

The present treatment of cancer in body cavities and parts that are cavity-like (termed "Body Cavity Cancer Treatment System" herein) eliminates the weaknesses and deficiencies of existing cancer treatment methods by implementing "Low Temperature Hyperthermia" in conjunction with ionizing radiation and/or chemotherapy. The combination has the potential for improving the effectiveness of cancer treatments by at least 2-4 times in the long term, while lowering the level of required radiation or chemotherapy medicine. While the Body Cavity Cancer Treatment System could be used to heat cancer cells to a killing temperature (46° Celsius and higher), it is believed that heating the cancer cells to a 5° C.-6° C. temperature increase over the body's ambient temperature (Low Temperature Hyperthermia) realizes significant benefits without incurring the risks of heating to the higher cell killing temperatures. Unlike other cancer treatment systems, the Body Cavity Cancer Treatment System does not directly kill or ablate the cancer cells with killing temperatures rather, the Body Cavity Cancer Treatment System stresses the cancer and cancer stem cells using Hyperthermia by keeping them at a nominal 42°-43° Celsius temperature for some period of time, for example 30 to 60 minutes, temperature and protocol dependent as set by the treating physician.

The Body Cavity Cancer Treatment System provides a systems level approach to cancer treatment that achieves extremely uniform temperatures inside the tissue surrounding the body cavity, thereby realizing optimal efficacy while avoiding harm or pain to the patient. This is accomplished by the inclusion of "target particles," such as nano-particles, into the body cavity along with the chemotherapy agent to enable the use of an externally generated energy field to cause heating of the chemotherapy agent and the surrounding tissue of the body cavity by activation of the nano-particles. The proper selection of the characteristics of the applied energy field enables precise control of the heat generated by the movement of the nano-particles. The Body Cavity Cancer Treatment System uses exactly matched or paired nano-particles having a given material composition and set of material properties in concert with a precisely defined electromagnetic field, in this case, a predominantly magnetic field. By using a magnetic field of certain properties and specifications, only the nano-particles heat while healthy tissue surrounding the region of cancer cells which contain the nano-particles does not heat.

An alternative to the procedure described above is the infusion of the chemotherapy agent into the bladder and the insertion of a "balloon" into the bladder. The balloon molds to the exact shape of the bladder, so nano-particles in a solution are put into the balloon, inflating the balloon and forcing the chemotherapy agent into the space between the balloon and the walls of the bladder. The solution of nano-particles in the balloon is heated via the application of an illumination energy field. The generated heat is transferred to both the bladder wall and the chemotherapy agent. At the end of the remaining portion of the procedure as noted above, the nano-particles are removed from the balloon and then the balloon is removed from the inside of the bladder, as is the chemotherapy agent. Alternatively, a fluid solution can be circulated through the balloon, without the use of the nano-particles, to maintain the temperature of the chemotherapy agent in the bladder.

In addition, the nano-particle delivery is non-invasive, meaning the nano-particles are contained in a fluid which is inserted into the body cavity and then removed after the procedure. For certain types of cancer, this has many attendant advantages: (A) the nano-particles do not enter the bloodstream, (B) control the exact concentration of nano-particles in a composite fluid usually containing a chemotherapy substance in solution (unless the protocol is pure ionizing radiation), (C) the known concentration of nano-particles enables much more precise heating illumination protocol, (D) the nano-particles are removed after the procedure and do not stay in the body, (E) pre-mixing of a chemotherapy agent with the nano-particle solution is easily achieved.

While the preferred embodiment disclosed herein is a treatment protocol for bladder cancer, the methods described herein can be used for other "cavity-like" organs or body structures. Body organs such as the colon, uterus, vagina, cervix, esophagus, stomach, and so on, that are naturally a cavity or that can be blocked off to form a temporary cavity, are viable body parts for this safe and efficacious treatment protocol. Catheter based balloons can be placed on either end of a cancerous region in a tubular like structure to only treat that segment of the "tube". Alternative body regions for treatment are also surgery developed cavities that leave a tissue void such as: remove a tumor in the brain, where the procedure fills the void with nano-particles and a chemotherapy agent, then heats the tissue and chemotherapy agent via the application of an externally generated magnetic field. Other surgical procedures that create a void, such as the removal of a tumor in the breast, could be treated using this approach.

There are a number of advantages that accrue using the treatment methods and protocol described herein:
Closed system for particle containment.
Particles are never introduced systemically.
Significant increase in the efficacy of the treatment.
Efficacy increases are upwards of 2-4 times; possibly significantly higher in certain cases.
This treatment re-uses existing chemotherapy and/or radiation treatment protocols and drugs in a new and novel method.
This treatment dramatically reduces the likelihood of burns, hot spots, cold spots, or inadvertent tissue heating.

BRIEF DESCRIPTION OF THE DRAWINGS

FIGS. 6A and 6B illustrate a block diagram of the Body Cavity Cancer Treatment Apparatus;

DETAILED DESCRIPTION OF THE INVENTION

Low Temperature Hyperthermia

Figure 1A:
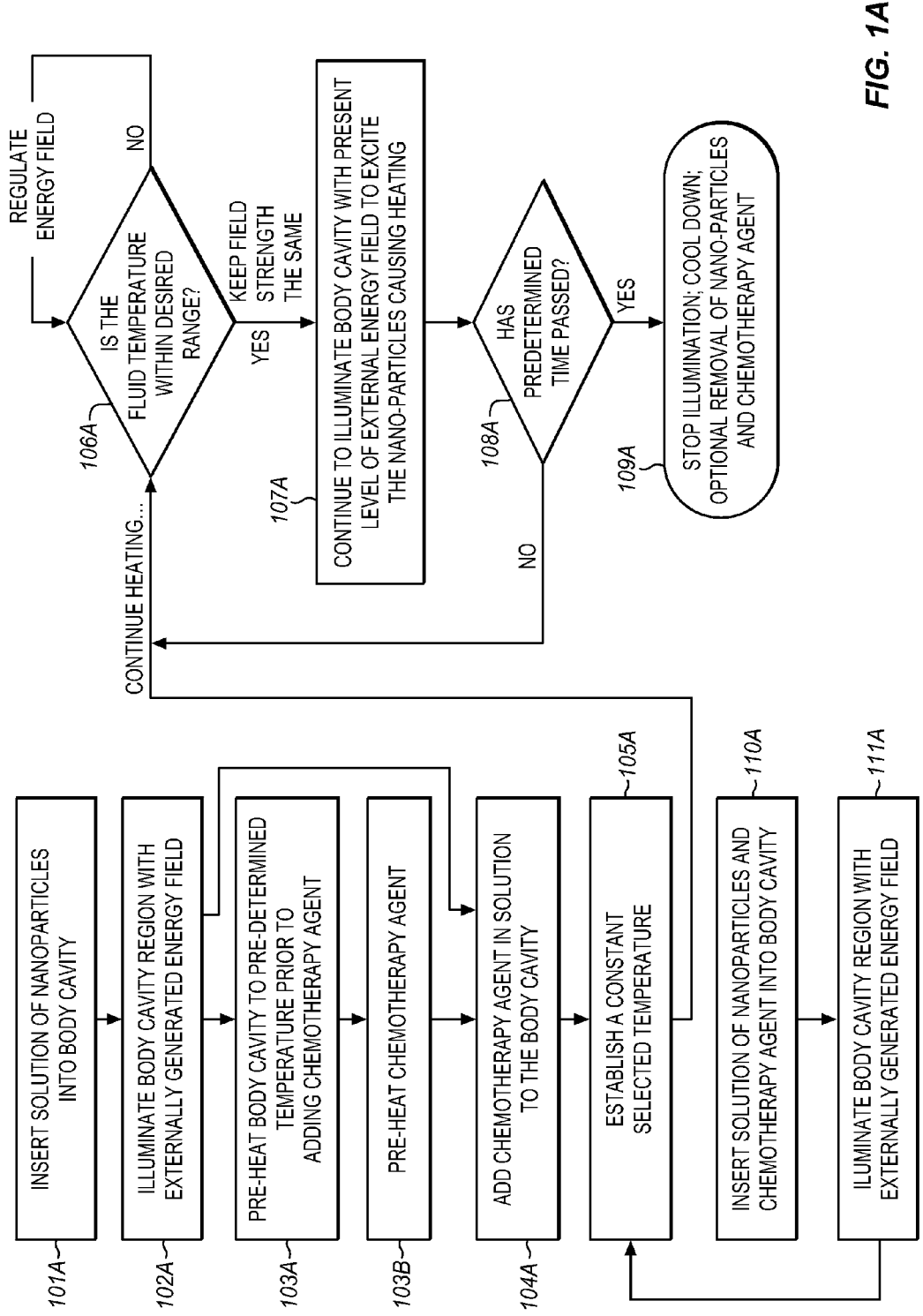
FIGS. 1A and 1B illustrate in flow diagram form the various steps of the protocol used to implement the present Body Cavity Cancer Treatment System, and a bladder cancer treatment implementation of this process, respectfully.

The combination of Low Temperature Hyperthermia with ionizing radiation and/or chemotherapy has the potential for increasing the effectiveness of cancer treatments by 2-4 times, as noted above, while lowering the level of required radiation or chemotherapy medicine. One additional benefit of Low Temperature Hyperthermia is re-oxygenation, where the level of oxygen in the tumorous regions is greatly increased. This is highly stressful to cancer and cancer stem cells in particular, which most decidedly prefer a hypoxic environment. Other significant biological benefits accrue when cancer is kept at a Low Temperature Hyperthermia state: acute acidification and reduction of Heat Shock Protein release (HSP). Other benefits accrue since ionizing radiation and Low Temperature Hyperthermia each affect different phases of the cellular reproductive process, M and S.

From the body ambient temperature of 37° C. to a target temperature of between 42° C. and 43° C., every degree increase above 37° C. increases the effectiveness of chemotherapy medicines. Such enhancement of chemotherapy agent effectiveness can change the treatment outcome from a 10 year complete cure rate of say 15%-20% without nano-particle based hyperthermia, typically to upwards of 50%-60% with nano-particle based hyperthermia for certain cancers, such as bladder cancer. This improvement in bladder cancer complete cure results is dramatic; it is expected as this technique is applied to other cancers and even other diseases that the similar efficacy and cure rates is evident.

Medicines, such as PARP inhibitors, interfere with the ability of cancer cells to self-repair damaged DNA in a given cancer cell. Thus, if the DNA in a given cancer cell is intentionally damaged, and the PARP inhibitor prevents the cancer cell from "self-fixing" the DNA, the cancer cell will die. However, PARP inhibitors are not very effective unless the ambient temperature is elevated to the 42° C.-43° C. range. Note that hyperthermia is also very effective at interfering with cellular DNA reproduction. Thus, being able to increase the ambient temperature of the cancerous region from 37° C. to 42° C.-43° C. is essential for PARP inhibitors to be effective in stopping cancer cells to self-repair their intentionally damaged DNA. Both the PARP Inhibitor and the Low Temperature Hyperthermia protocol, individually and in concert, impact/prevent the cancer cell's ability to repair the damaged cancer cell DNA. At the moment, it is believed that concurrent-heating of the cancerous region is likely the most beneficial protocol but there may be reasons why a pre- or post-heating protocol relative to the timing of radiation or chemotherapy is preferred.

The nano-particles are activated by a precisely crafted energy field to provide illumination of the nano-particles with the minimum energy that is required to create the selected effects. The energy field characteristics are selected from the characteristics of energy fields including: field type, frequency, field strength, duration, field modulation, repetition frequency, beam size and focal point, that are required to energize the nano-particles in a selected manner in the portion of the target living organism that is being treated. In addition, the mapping of characteristics of the energy field provides great flexibility and enables the concurrent use of multiple types of nano-particles.

It is important to note that the activation of nano-particles by the Body Cavity Cancer Treatment System is highly deterministic, meaning that a given particle is optimally activated or excited by a given energy field of pre-defined characteristics. Generic or random field excitations do not optimally excite a given particle. The field excitation of a nano-particle is considered to be the "input energy" or "input driving function" of the system. In general, the "input energy" is converted by the nano-particles to an "output energy" which is a thermal output.

Operation of the Body Cavity Cancer Treatment System

Figure 1B:
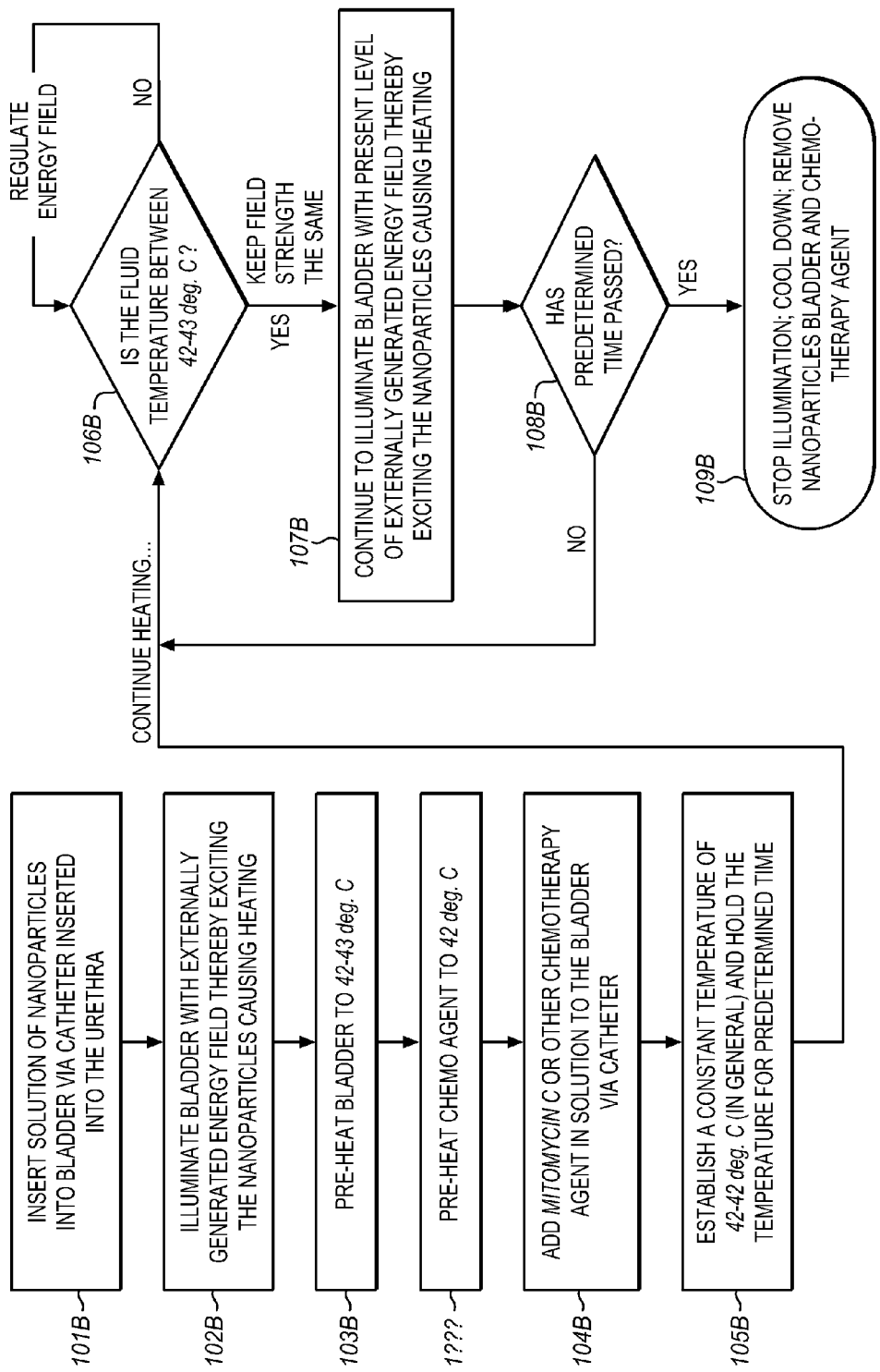

FIG. 1A illustrates in flow diagram form the typical operation of the present Body Cavity Cancer Treatment System 40, while FIG. 1B illustrates in flow diagram form the typical operation of the present Body Cavity Cancer Treatment System 40 as implemented in a bladder cancer treatment protocol.

At step 101A of FIG. 1A, a solution of nano-particles is inserted into the target body cavity by whatever technique is appropriate for use by medical personnel. At step 102A, the body cavity is illuminated by the application of an externally generated energy field, such as a magnetic field generated by the apparatus of FIGS. 2-5, 6A, and 6B. The energy field is maintained to slowly heat the body cavity at step 103A to a predetermined temperature. At step 104A, one or more chemotherapy agents are added to the body cavity, with the chemotherapy agent optionally being preheated to a predetermined desired temperature at step 103B. At step 105A, the Body Cavity Cancer Treatment System 40 establishes a constant selected temperature in the body cavity and/or chemotherapy agent by the energy controller 62 regulating the applied energy field via control computer 409, waveform sources 403, 601, amplifier 404 and current sense circuit 614. The process then advances to steps 106A-108A where the energy controller 62 of the Body Cavity Cancer Treatment System 40 tests, via temperature sensors 616 or 617 and control computer 409, to determine whether the temperature of the body cavity/chemotherapy agent is within predetermined limits and, if not, regulates the intensity of the magnetic field to achieve the desired temperature. This process of maintaining the desired temperature continues for a predetermined time until the energy controller 62 of the Body Cavity Cancer Treatment System 40 at step 108A computes that the predetermined time has elapsed, at which point, processing advances to step 109A where the magnetic field is removed, the body cavity and chemotherapy agent are allowed to cool and the nano-particle solution and chemotherapy agent are typically removed from the body cavity.

Alternatively, at step 110A, a mixture of a solution of nano-particles and one or more chemotherapy agents are added to the body cavity, with the mixture optionally being preheated to a predetermined desired temperature. At step 111A, the body cavity is illuminated by the application of an externally generated energy field, such as a magnetic field generated by the apparatus of FIGS. 2-5, 6A, and 6B. Processing then advances to step 105A, where the energy controller 62 of the Body Cavity Cancer Treatment System establishes a constant selected temperature in the body cavity and/or chemotherapy agent and steps 106A-109A are executed as described above.

The treatment protocol is defined by the physician, who selects the time and temperature parameters. In addition, the solution of nano-particles and one or more chemotherapy agents may be combined, preheated, and then inserted into the body cavity. This reduces the treatment time and simplifies the process by implementing only one insertion step.

Treatment of Bladder Cancer

Figure 7:
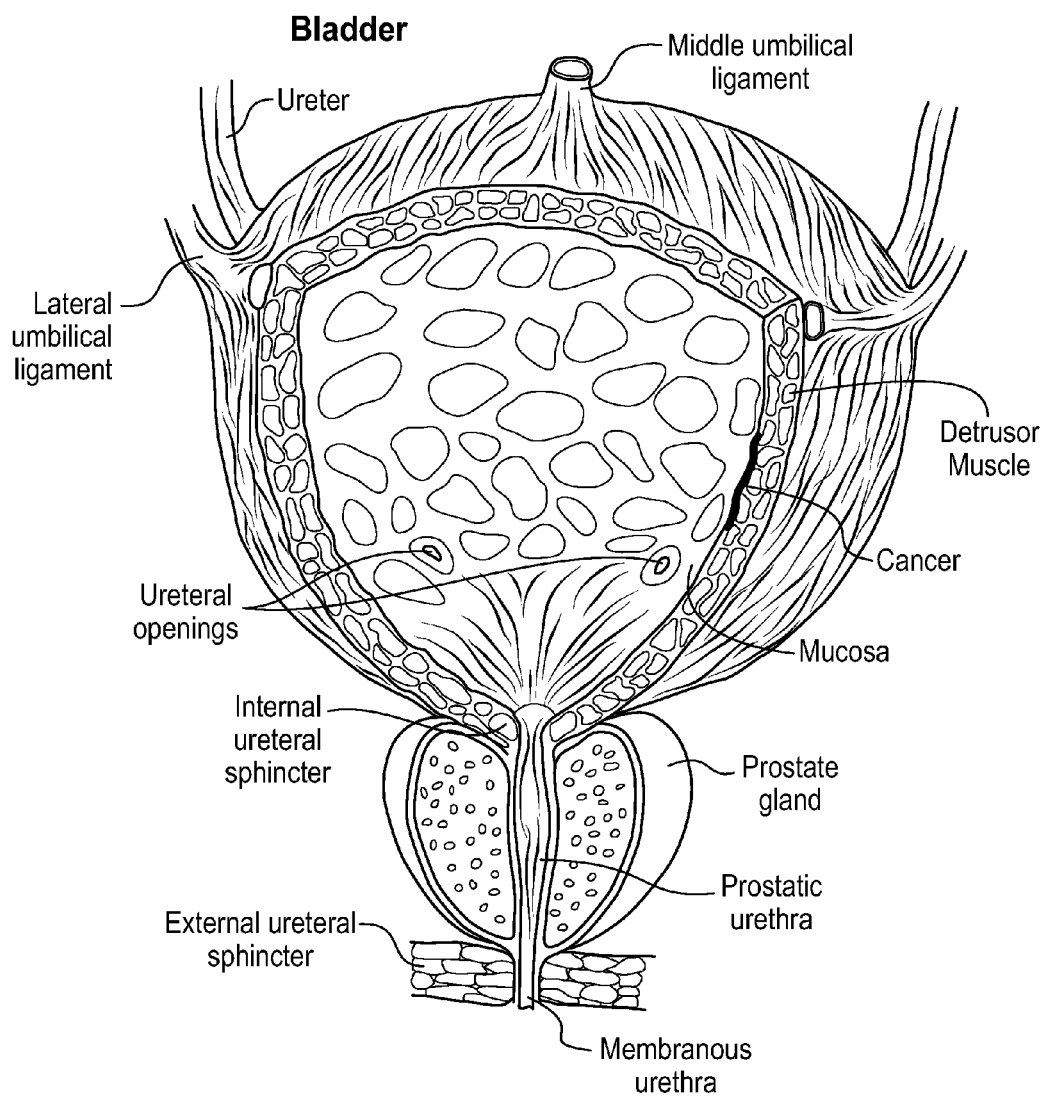
FIG. 7 illustrates in cross-section view of the human bladder, illustrating the major components thereof.

The process just described can be implemented for various body cavities as noted above and FIG. 1B provides additional details to the flowchart of FIG. 1A to show how this procedure can be customized for a particular body cavity and cancer type. In particular, FIG. 7 illustrates a cross-section view of the human bladder, illustrating the major components thereof. The detrusor muscle is a layer of the urinary bladder wall made of smooth muscle fibers arranged in spiral, longitudinal, and circular bundles. The bladder is held in place in the abdomen by the Lateral Umbilical Ligament, and the Middle Umbilical Ligament. The bladder receives urine via the Ureter and expels urine through Ureteral openings which feed the Urethera. One form of bladder cancer is termed "Non-Muscle Invasive Bladder Cancer" which is sited on the surface of the bladder interior and typically is no deeper than 500 microns in through the mucosa. Thus, the insertion of chemotherapy agents into the bladder ensures that the chemotherapy agents come into contact with the cancer.

When the bladder is stretched, this signals the parasympathetic nervous system to contract the detrusor muscle. This encourages the bladder to expel urine through the urethra, which passes through the Prostate Gland. For the urine to exit the bladder, both the autonomically controlled internal urethral sphincter and the voluntarily controlled external urethral sphincter must be opened. Problems with these muscles can lead to incontinence. If the amount of urine reaches 100% of the urinary bladder's capacity, the voluntary sphincter becomes involuntary, and the urine is ejected instantly. The urinary bladder usually holds 300-350 ml of urine. As urine accumulates, the wall of the bladder thins as it stretches, allowing the bladder to store larger amounts of urine without a significant rise in internal pressure.

The urge to urinate usually starts when the bladder reaches around 25% of its working volume. At this stage it is easy for the subject, if desired, to resist the urge to urinate. As the bladder continues to fill, the desire to urinate becomes stronger and harder to ignore. Eventually, the bladder will fill to the point where the urge to urinate becomes overwhelming, and the subject will no longer be able to ignore it.

At step 101B of FIG. 1B, a solution of nano-particles is inserted into the bladder by passing a catheter through the Urethra, with the volume of fluid being selected to not fill the bladder, leaving room for the chemotherapy agent and normal urine production during the treatment timeframe. At step 102B, the bladder is illuminated by the application of an externally generated energy field, such as a magnetic field generated by the apparatus of FIGS. 2-5, 6A, and 6B. The energy field is maintained to slowly heat the bladder, via the illumination of the nano-particles, at step 103B to a predetermined temperature, which is typically 42° C.-43° C., prior to the addition of a chemotherapy agent. A fiber optic thermal sensor 617 can be used with a computer controlled algorithm 409 to manage and adjust the applied field strength via a feedback control signal 602 applied to the amplifier 404. At step 104B, one or more chemotherapy agents, such as Mitomycin-C are added to the bladder, with the chemotherapy agent optionally being preheated to a predetermined desired temperature, which is typically 42° C. At step 105B, the energy controller 62 of the Body Cavity Cancer Treatment System establishes a constant selected temperature, which is typically 42° C.-43° C., of the fluid located in the bladder and the surrounding tissue for a predetermined time. The process then advances to steps 106B-108B where the energy controller 62 of the Body Cavity Cancer Treatment System tests to determine whether the temperature of the bladder/chemotherapy agent is within predetermined limits and, if not, regulates the intensity of the magnetic field to achieve the desired temperature. This process of maintaining the desired temperature continues for a predetermined time, typically 60 minutes, until step 108B computes that the predetermined time has elapsed, at which point, processing advances to step 109A where the magnetic field is removed, the bladder and chemotherapy agent are allowed to cool and the nano-particle solution and chemotherapy agent are typically removed from the bladder by urination or flushing.

In some situations, it may be desirable to not have the nano-particles touch or come into contact with human tissue, to include the bladder interior lining (mucosa). At the same time, it is still desirable to heat the interior of the bladder (or human tissue) to enhance the effectiveness of the chemotherapy agent or radiation, either or both intended to kill harmful cancer and cancer cells. In the case of bladder cancer, it is desirable to enhance the efficacy of chemotherapy agents such as Mitomycin C (MMC). An alternative to the procedure described above is the infusion of the chemotherapy agent into the bladder and the insertion of a "balloon" into the bladder. By using a balloon based catheter assembly, the nano-particles can be both heated and still retain their physical isolation from human tissue—the bladder lining. The balloon molds to the exact shape of the bladder, so nano-particles in a solution are put into the balloon, inflating the balloon and forcing the chemotherapy agent into the space between the balloon and the walls of the bladder. The solution of nano-particles in the balloon is heated via the application of an illumination field. Alternatively, a fluid solution can be circulated through the balloon, without the use of the nano-particles, to maintain the temperature of the chemotherapy agent in the bladder. The generated heat is transferred to both the bladder wall and the chemotherapy agent. At the end of the remaining portion of the procedure as noted above, the nano-particles are removed from the balloon and then the balloon is removed from the inside of the bladder, as is the chemotherapy agent.

Balloon Catheter Process Details

Figure 17A:
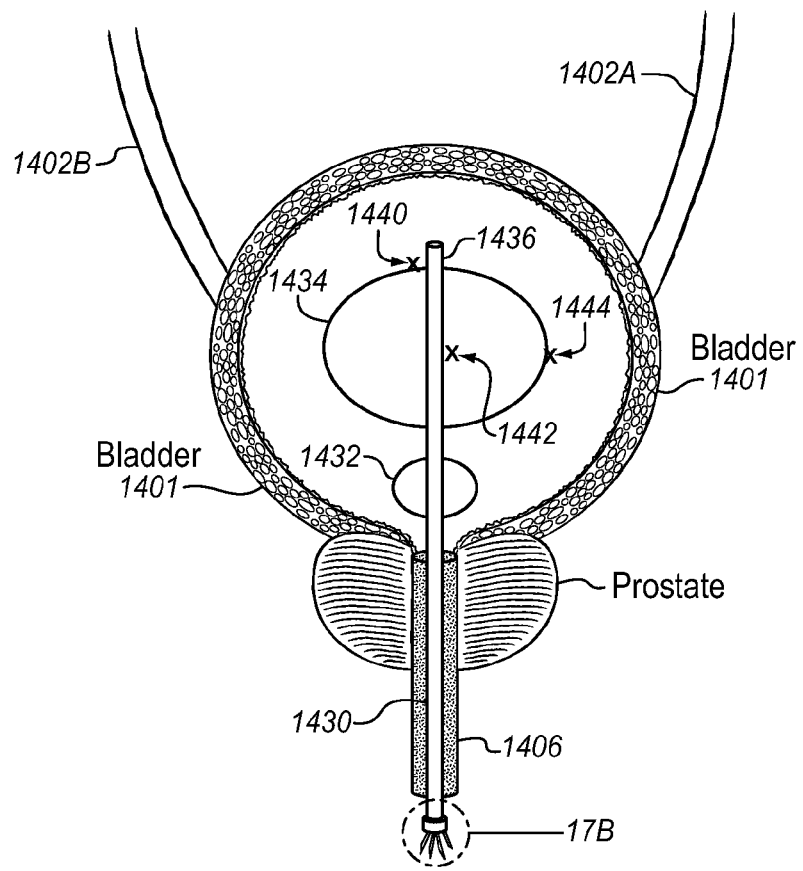
FIG. 17A, 17B depicts a catheter in a human bladder with associated catheter and human anatomy descriptions.
Figure 17B:
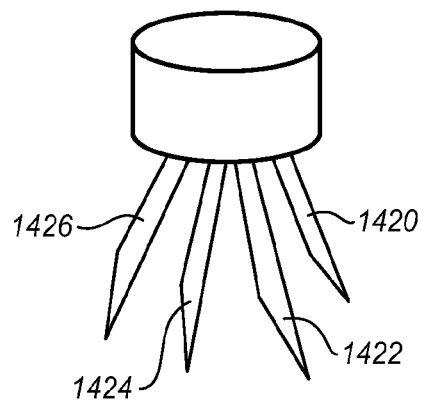

FIG. 17 shows a human bladder 1401 with a catheter 1430 already inserted into the bladder 1401. Catheter assembly (1430, 1432, 1434, 1436) is inserted into bladder 1401, which is connected to the kidneys (urine flowing into the bladder 1402 via ureters 1402A and 1402B), with the urethra 1406 being the means for draining the bladder 1401 (via urination) as well a passageway for inserting the catheter assembly. The catheter 1430 has holes or tubes along its length which are called lumens. These lumens are in the cross section of the tubular portion of the catheter 1430. This particular catheter has four sets of lumens; the number of lumens is generally restricted only by the size of the "tube" containing the lumens. The sizing of the "tube" is measured in units termed "French" and, for human bladder use; the catheter is typically between 18 to 24 French. A larger French number means the "tube" has a larger diameter.

Catheters are often constructed of extruded silicone or latex materials (the shaft is 1430, 1436 which is equipped with lumens 1420, 1422, 1424, 1426). The balloons (1432 and 1434) are often made via a "blown" methodology. Together, the extruded shaft 1430 plus the balloons 1432, 1434 are constructed to make the entire catheter assembly. Thermocouples 1440, 1442, and 1444 are added to enable a temperature control feedback mechanism to the energy controller 62 for managing the strength of the magnetic field, which in turn controls how warm the nano-particles get. For example, input lumen 1426 is connected to the output 1436 which is located at the tip of the catheter 1430 above the large balloon 1434. This particular lumen assembly is used to put fluid into or to take fluid out of the bladder 1401. At the beginning of the procedure, lumen pair 1426 could also be used to remove any excess urine and then, prior to the procedure starting it could be used to insert Mitomycin C, a chemotherapy agent, into the bladder 1401.

The combination of both heat and the chemotherapy agent are the basis of a treatment protocol that has significantly higher efficacy than just a chemotherapy agent alone (as is now practiced by urology oncologists). By adding heat to the bladder tissue and cancer for a nominal one hour treatment time frame, the efficacy of MMC to treat bladder cancer is quite dramatic—the ten year complete cure rate in increased from 15% to upwards of 53%.

Lumen pairing, 1424 (input) to 1434 (output into the larger balloon 1434), is used for instilling nano-particles into the balloon 1434. One advantage of using a balloon to contain the nano-particles is that the ureters 1402B and 1402A do not dilute the nano-particle concentration with urine from the kidneys. Thus, the nano-particle concentration is constant and it simplifies the heating control algorithm.

The MMC (chemotherapy agent) is instilled via lumen 1426 and output 1436 directly into the bladder 1401. Lumen 1422 is used to inflate the small balloon 1432, typically with air; the purpose of this small balloon 1432 is to keep the catheter 1430 seated in the bladder 1401 during the treatment time frame. It is desirable to keep the larger balloon 1434 off of the bladder wall since this balloon 1434 is the heat source and it is desirable to not have the warm balloon surface touching the balder wall to prevent either burns or excessive heating.

In this example, lumen 1420 is used to link three thermocouples 1440, 1442 and 1444 which sense the temperature in three different locations to the energy controller 62. Thermocouple 1440 senses the temperature of the fluid (MMC with some urine) in the bladder 1401 while thermocouple 1442 senses the temperature in the center of the balloon 1434 which holds the nano-particles (it is fed thru lumen 1420). It is important to check the temperature at the center of the balloon 1434 because it enables the energy controller 62 to know what the maximum temperature is and then what the thermal gradient is across the balloon 1434. The thermocouple 1444 is located on the outer edge of the balloon 1434 and is used to ensure that the external balloon temperature is safe for the bladder 1401 should it ever touch the bladder wall. Mathematically, the temperature difference between thermocouples 1442 and 1444 can be determined, as a gradient, and this calculation can be compared to measured temperatures as an error check to ensure no thermocouples are mis-reporting their data. Typically, thermocouple 1444 measures 2° C.-4° C. warmer than the temperature on the bladder wall. The thermocouples used are typically fiber optic based, using a Gallium Arsenide (GaAs) crystal which vibrates at a given frequency for a given temperature. This vibration frequency is sensed and is then converted to a temperature measurement and reported to the systems electronics in a temperature to magnetic field strength feedback loop. Fiber optic sensors are important since they are not affected by the presence of a magnetic field which is used to excite the particles in Brownian motion thereby causing frictional based heating.

Figure 18:
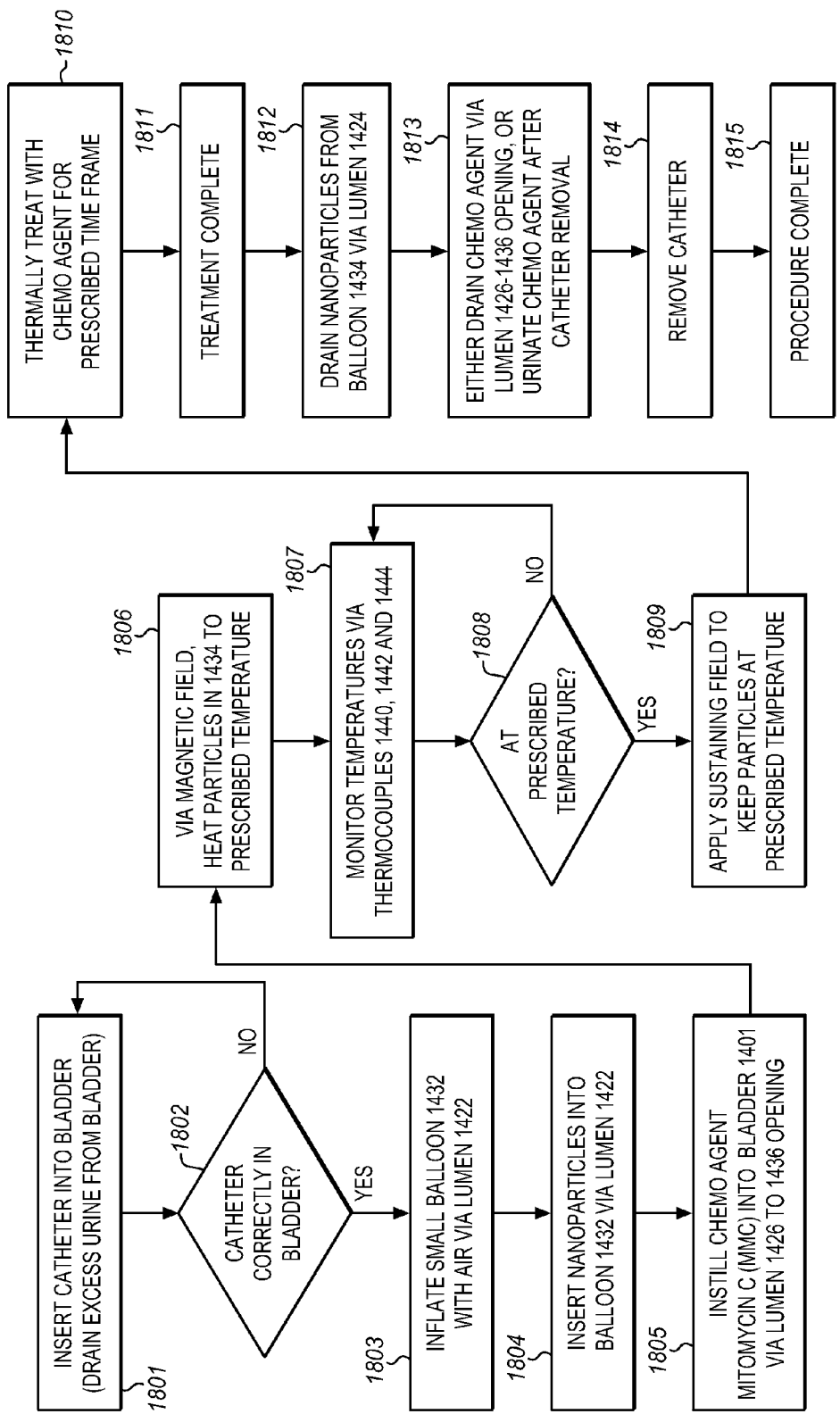
FIG. 18 describes in flowchart form the process of using a catheter to instill particles into the bladder but retaining particle isolation from the bladder itself.

FIG. 18 illustrates in flowchart form one process for nano-particle heating. At step 1801, the catheter 1430 is inserted into the bladder 1401 and, at step 1802 it is determined to be positioned in the correct location in the bladder 1401. At step 1803, the small balloon 1432 is inflated (typically with air); this small balloon 1432 keeps the catheter 1430 properly installed as well as helping to keep the large balloon 1434 holding heated nano-particles from touching the bladder interior lining.

This treatment is largely for Non-Muscle Invasive Bladder Cancer (NMIBC) which is polyp like and grows inward into the bladder wall of the bladder 1401 and, in general, has a stalk like structure. Current thermal projections indicate that the thermal treatment needs to penetrate only 0.5 mm into the bladder wall to treat Ta and T1 NMIBC types of bladder cancers. At step 1404, nano-particles are inserted into the larger balloon 1434 via lumen 1424. At step 1805, the chemotherapy agent, such as Mitomycin C (MMC), is inserted into the bladder 1401 directly via lumen 1426 to opening 1436. Next, the magnetic field is applied as previously described herein. At step 1806, the nano-particles are heated in balloon 1434 in the prescribed manner. The overall system temperatures are monitored by the energy controller 62 via thermocouples 1440, 1442 and 1444 at step 1807. Note that either or both the MMC and the nano-particles can be pre-heated to the nominal body temperature of 37° C. prior to insertion via catheter 1430 as described above. This pre-heating of the two materials shortens the overall procedure time-frame since they are at body temperature at insertion.

At step 1808, the energy controller 62 checks one or more of the thermocouples to ensure they are at the proper operating temperature and if too warm, the feedback to the amplifiers 404 feeding current into the coils 601, 602, is turned down which further lowers the magnetic field generated thereby reducing the heating rate. Once at the desired operating temperature, at step 1809, the magnetic field is managed to keep the nano-particles at the prescribed temperature, typically 42° C.-43° C. for low temperature non-ablative therapy.

At step 1810 the treatment protocol, using heated nano-particles and chemotherapy agent, is managed for the doctor prescribed timeframe, but typically for an hour at the therapeutic temperature. It is believed that a 1° C. temperature increase can reduce the treatment time frame by ½ and a 2° C. increase in temperature is a ¼ reduction in heating time frame. However, the pairing of temperature with time is to be determined and is ultimately the responsibility of the treating physician.

At step 1811, the treatment is done and the "reverse" process is now effected. At step 1812, the nano-particles are drained out of balloon 1434 via lumen 1424. And at step 1813, the chemotherapy agent can be drained via lumen 1426 or the catheter 1430 can be pulled and the patient urinates out the chemotherapy agent. This is how the chemotherapy agent is removed today. There is an advantage to removing the chemotherapy agent via catheter 1430 due to how caustic the chemotherapy agent is to the urethra and its lining. At step 1814, the catheter 1430 is removed and at step 1815 the procedure is completed.

Cancer Cells and Hyperthermia

For cells that are dividing, four (4) phases exist—M phase, $G_1$-phase, S-phase and $G_2$-phase with radiation and hyperthermia each affecting different phases. Hyperthermia is most sensitive in the last half of the S-phase, DNA Reproduction. The next cellular phase which hyperthermia impacts are the M-phase, Cell Division. However, radiation sensitivity is high in the M-phase (Cell Division) but low in the S-phase (DNA Reproduction). Thus, hyperthermia is complimentary with radiation—particularly for the S-phase which is the DNA reproduction phase. That is why Low Temperature Hyperthermia (LTH) is so effective when combined with Radiation. As previously mentioned, PARP Inhibitors affect the DNA repair stage, similarly where hyperthermia works and, hyperthermia enhances the effectiveness of chemotherapy at an effectiveness doubling rate for every degree above body ambient.

The nano-particles that heat in a magnetic field must exhibit magnetism and are generally ferromagnetic in nature. Materials such as magnetite $Fe_3O_4$ and maghemite $Fe_2O_3$, when produced in nanometer sizes, will heat in magnetic fields of time varying nature. These AC or Alternating Current magnetic fields are typically in the kilohertz frequency range but can also be in the megahertz range. For the preferred Brownian heating mode, the optimal frequency range is 30,000 to 100,000 hertz (30-100 KHz). The particle sizes are sufficiently small in diameter to be characterized as predominantly a single domain.

Magnetic excitation is via an Alternating Current (AC) driven, where the change of the phase of the wave going from positive to negative to positive (and so on) causes changing magnetic alignments in the nano-particles which in turn cause heating. The changing magnetic alignment causes a portion of the induced energy to be converted as heat (by the nano-particles). The two forms of magnetic heating involve: One, friction based heating created by the nano-particles' movement with respect to the cytoplasm (for instance Brownian) and, Two, heating which is magnetic domain based (Neel), where the nano-particles are stationary and the magnetic domains in the nano-particle are changing. Depending on the particle size relative to the excitation frequency, the heating could involve both Brownian and Ned modes.

The first, friction based, is called Brownian heating and the nano-particle physically rotates, causing mechanical friction based heating. Because the nano-particle is physically rotating, there is a relaxation time that is optimal for maximal nano-particle heating where the relaxation time is related to both the nano-particle size and the excitation frequency. This unique pairing of nano-particle size with frequency causes optimal heating. In this case, the nano-particle size, composed of the core plus any coatings, is called the hydrodynamic diameter, and it is this composite size that is important for Brownian heating. Additionally, the material's properties, such as magnetization and anisotropy affect where and how well it heats.

The second method, where just the magnetic domains are changing, is called Ned heating. In this case, a very narrow size and corresponding frequency match enables heating; and, any slight changes in those parameters can cause the nano-particle to not heat at all. It is this very sensitivity that makes Ned heating the less preferred approach.

Other modes of magnetic nano-particle heating include hysteresis and Rayleigh, where these modes are usually reserved for significantly bigger particles, say greater than 50 nanometers in size. In general, the single domain modes, where the nano-particles are smaller, less than 50 nm in general, having Brownian and/or Ned heating, are preferred. Presently the preferred magnetic field generation mechanism is a wire coil or coils, which projects magnetic fields into tumorous regions, in which the fields create a uniform volume in the region where the cancer resides. Relatively uniform fields across a tumor is important for minimizing hot spots (we assume that nano-particle uptake is relatively uniform across a tumorous region).

The Treatment Table/Machine

FIGS. 2-4, 6A and 6B illustrate the Body Cavity Cancer Treatment Apparatus 40 that is used to illuminate the patient with an externally generated magnetic field. Two coils 401, 402, positionable above and below the patient 407, create a magnetic field between the two coils 401, 402 which harmlessly passes through the body of the patient 407. This magnetic field excites the 20 nm nominal sized magnetite Fe3O4 nano-particles that have been inserted into the bladder cavity of the patient 407 and causes them to heat up, predominantly via Brownian excitation. Brownian heating is a result of the particles physically rotating at the rate of the excitation frequency, in this case, 40 KHz. The level of nano-particle heating is based on the level of electrical current in the coils 401, 402 which then produce a given magnetic field strength of a prescribed level.

Figure 3:
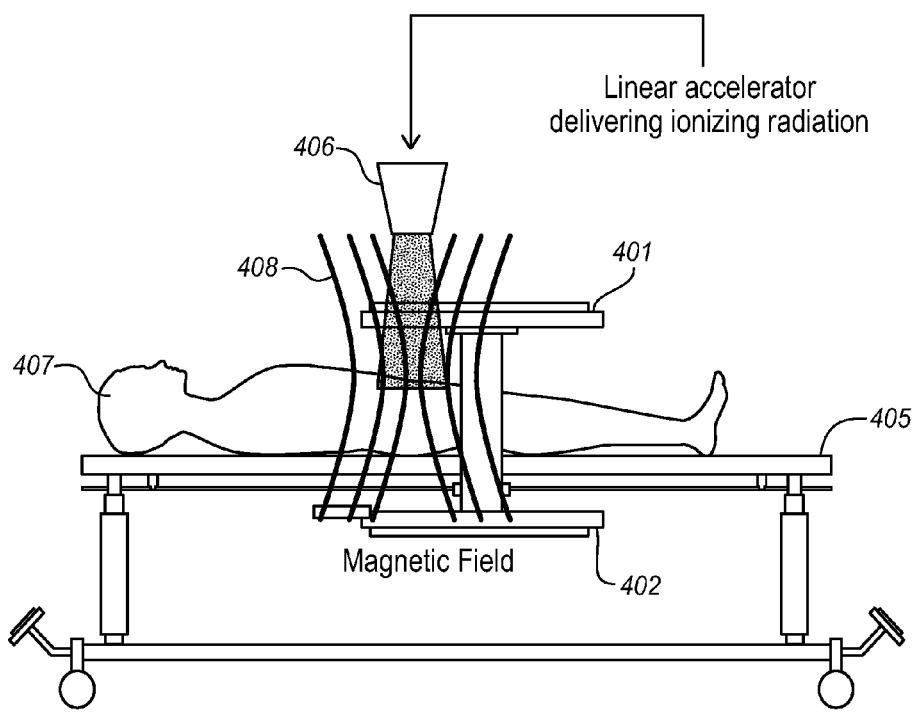
Figure 4:
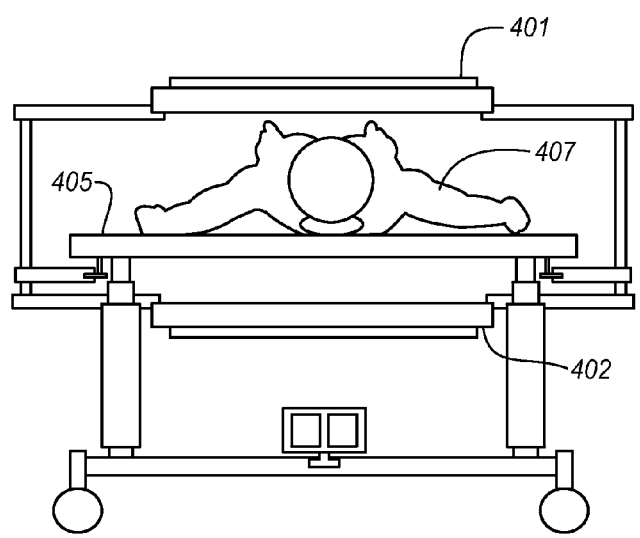

FIGS. 3 and 4 show how the open coil ring enables the passage of ionizing x-ray radiation 408 for an additional treatment protocol. Again, the preferred embodiment of the Body Cavity Cancer Treatment Apparatus 40 is the generation of a magnetic field to illuminate magnetic field susceptible nano-particles. However, an electric field with electric field particles or substances can also be used. As an example, MMC is dipolar and may heat in an electric field. If so, this would remove the need for nano-particles.

Figure 2:
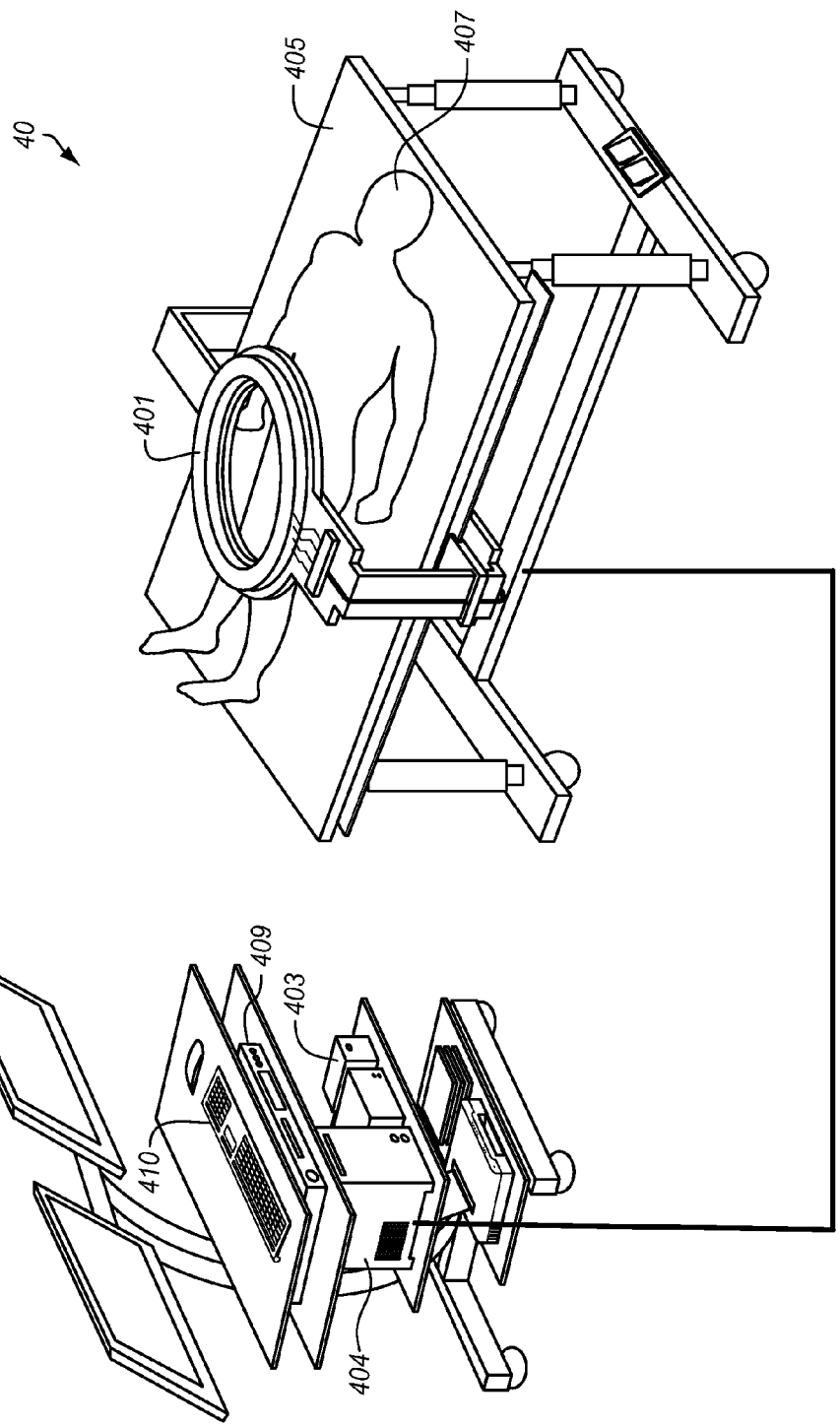
FIGS. 2-5 illustrate the apparatus that is used to illuminate the patient with an externally generated magnetic field.
Figure 5:
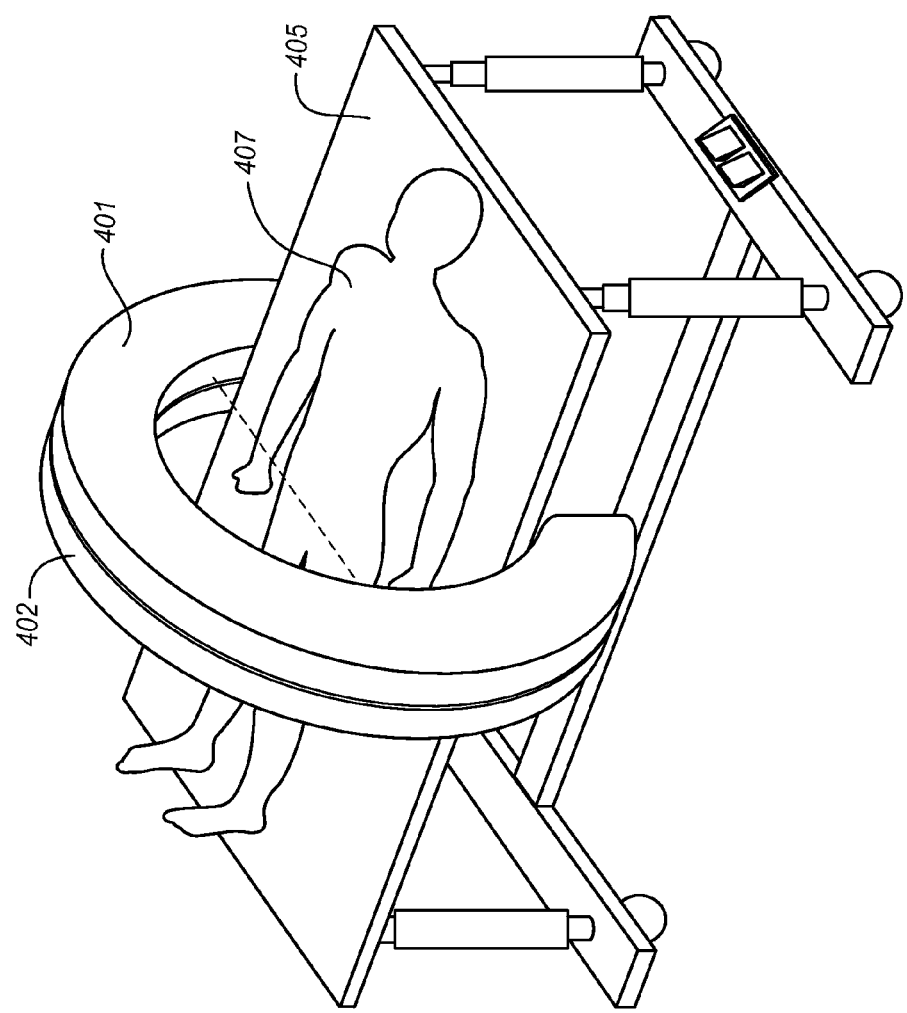

FIGS. 2-4 show a patient (living organism) 407 lying face up on table 405 with the coil assembly 401, 402 of the Body Cavity Cancer Treatment Apparatus 40 sliding over the body 407 to optimally align the coil pair 401, 402 over the region of the patient's body to be illuminated (the region that contains nano-particles). Note, while not directly visible in this perspective of FIG. 2, there is a bottom coil 402 of the Body Cavity Cancer Treatment Apparatus located under the table sliding in concert with the upper coil 401 going over the patient 401. FIG. 6B illustrates a cross-section diagram of the Body Cavity Cancer Treatment Apparatus, which shows the two coils as well as the target area where the magnetic field is focused on the patient who is on the table as well as the surrounding area of reduced magnetic field and a surrounding buffer area. This conceptualization of the Body Cavity Cancer Treatment Apparatus 40 uses a toroid shaped coil having a coil diameter of 60 centimeters, or 23.6 inches. In practice, the coils 401, 402 can be of any size or even shape, such as square. Other coils 401, 402 could also be added in an orthogonal plane as shown in FIGS. 4 and 5 (as the sole coil) to enhance the size of the uniform heating region. The "first winding, upper coil" to "first winding, lower coil" spacing is 30 cm in this concept (which can be increased to accommodate larger people). An increased spacing of the coils 401, 402 would either mean a larger coil diameter or more drive current for the existing coil diameter (to compensate for the fields falling off or being "stretched" by increasing the spacing) to produce the same magnitude energy field. Alternatively, lower field strength can be used with the caveat that slightly more time is required to reach the target temperature.

Figure 6A:
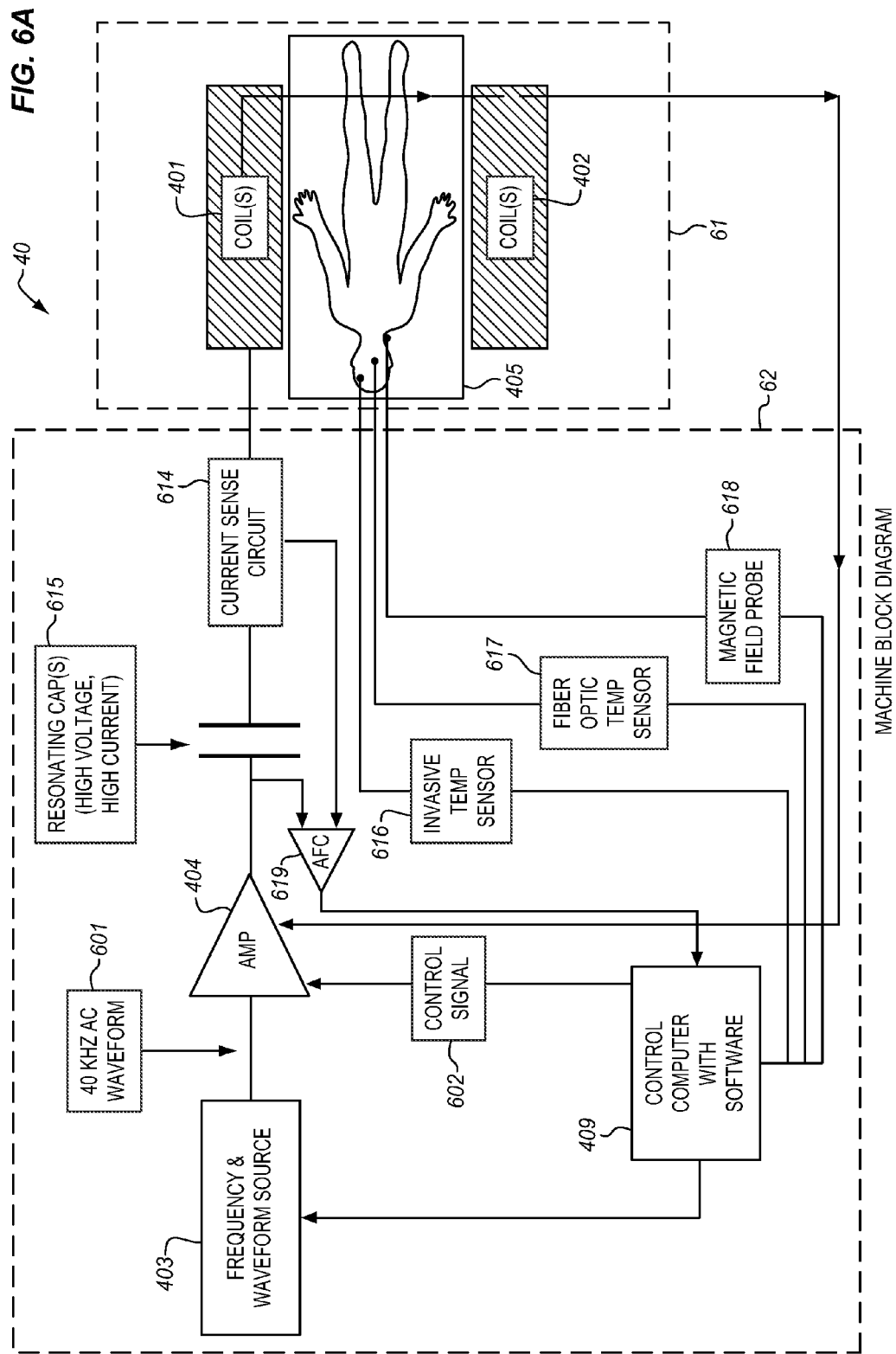

FIG. 2 also shows an implementation of the Body Cavity Cancer Treatment Apparatus 40 which has an electronics equipment rack which contains the signal source 403, signal amplifier 404, control computer 409 with software, user input keyboard 410 with GUI touch screen and fiber optic temperature measurement system 617, as also illustrated in schematic form in FIGS. 6A and 6B. An AFC circuit 619 is also provided to bring energy controller 62 back to resonance by sensing the phase between the voltage and the current and selecting a new excitation frequency to get back to the resonance driving frequency. The control computer 409 is used by the physician to select the characteristics of the generated energy field, as described above, to match the characteristics of the nano-particles that are inserted into the cavity, as well as to define the treatment protocol: temperature, duration, and heating profile. Alternatively, invasive temperature sensor 616 would have sensors on the body of the patient 407. Separately, for a bladder heating assembly using a Foley catheter to administer both the nano-particles and the chemotherapy agent such as Mitomycin-C (MMC), a fiber optic temperature probe can be inserted into the bladder cavity to measure the treatment temperature of the fluid in the bladder. Finally, a magnetic field probe 618 can be used to measure the energy field within the cavity.

The magnetic volumetric region of quasi uniform fields is on the order of 30 cm in body thickness dimension by an area of 35 cm in body width by 35 cm in body length, which is 11.8 inches in body thickness by 13.8 inches in body width by 13.8 inches in body length. Overall, this is 36,750 cubic centimeters of "uniform field" volume or 2,247 cubic inches of "uniform field" volume. It is believed that this uniform field volume is sufficient for virtually any type of regionally located cancer that hasn't metastasized.

The coils 401, 402 of the Body Cavity Cancer Treatment Apparatus 40 require other passive components in order to allow them to efficiently and safely work with a given amplifier design. Most amplifiers 404 prefer a "real" input, in terms of the input impedance presented by the coil load. To realize "real" impedance in the Body Cavity Cancer Treatment Apparatus 40, the inductive reactance of the coil must be matched with an equivalent series connected capacitor 615 to cancel out the reactive voltages. This is to stay in compliance with the amplifier's operating requirements. As shown in FIG. 6A, the coils 401, 402 and capacitor 615, connected in series, realize a series LC circuit which is resonant at the desired illumination frequency. The series LC circuit, at the resonant illumination frequency, has zero reactance and only the AC resistance of the coils 401, 402 and the ESR (Equivalent Series Resistance) of the capacitors 615.

At resonance, what are left in the coils are AC resistive losses. The capacitors 615 have an Equivalent Series Resistance, which is frequency dependent; in order to get the Equivalent Series Resistance low, a number of capacitors need to be put into a parallel configuration (if the capacitors are at the system input); or, alternatively, as shown in FIG. 6B, the capacitors are distributed into the windings of the sub-coils. Again, the "matching circuit" uses capacitors to cancel out the inductive reactance of the coil assembly in order to reduce the reactive voltage to "zero" at resonance. In addition, at least one capacitor per coil or sub coil, if broken into sub coils, should be a variable capacitor to make sure all of the coils are resonant at the same frequency. For a variety of reasons, the selected frequency of operation of the Body Cavity Cancer Treatment Apparatus 40 is typically 40,000 hertz (40 KHz).

How the coil is wound and how the wires are juxtaposed to each other significantly affects the AC resistance or ESR Equivalent Series Resistance. This also affects the field strength generated for a given current into the coil windings. If a gap of 0.6 to 0.75 inches (around 1 cm) is placed between the axial windings, the ESR can be significantly reduced. Presently, at 77 amps RMS of drive current, the AC resistance of the coil is around 0.3 ohms at 40 KHz. Radially, the wires (or rather the insulation of the wires) can be touching without much effect on a person's skin.

Other coil related issues must be managed, such as ensuring that corona inception is not possible at the given air pressure and temperature. Corona inception is where the voltage gradient or field strength is of a sufficient level, say 24.1 Kv per cm, at 6,000 feet altitude and 40° C.—if the voltage gradient on the outer edge of the wire insulation or say between the edges of two wires' insulation is greater than 24.1 Kv/cm—then a corona inception is possible. Corona is essentially the breakdown of the air gap and is evidenced by purplish or orangish light, a staccato like sound and then eventually a voltage arc.

Selections of the insulation, the spacing, the number of turns, how the coil is wound and so on all affect the likelihood or risk of corona. One key method of reducing the level of the voltage gradients is to add air gaps between the wires in the axial direction (direction of the human body 407 in FIG. 5) and to break up the coil up into two coils, separated by both air and a plastic dielectric. These two sub-coils are not spaced sufficiently to garner the Helmholtz condition.

The B field, the H field is vectorially parallel to the human 407. The nominal treatment volume is on the order of a cylinder 10 cm in radius and about 20 cm long. The length of the uniform field volume is dependent on how far apart the two sub coils are spaced (again, not at a Helmholtz condition). This field volume is sufficiently large to have a uniform field for the treatment volume (particle balloon volume) and sufficiently large enough to not cause difficulty in centering this region onto the patient. There may be some eddy current heating advantages to the coil body relationship as shown in FIG. 5. This is due to the volume based integral of field lines being captured by the body—a Helmholtz design, where the two coils are farther apart, and cause more lines of flux to be captured by the body 407—hence have higher unintentional eddy current heating.

Bladder Heating Protocol

Using computer models, which are highly predictive of actual nano-particle heating in a magnetic field, the following treatment protocol has been developed which enables a significant improvement over the prior art. In addition, the efficacy of this protocol is substantially improved over existing protocols to include the following benefits: much safer; no heating hot spots or tissue burns; no inadvertent heating of adjacent tissue; more uniform heating profile making the efficacy more uniform; lower cost; and provide better patient comfort.

The following description examines the feasibility of using nano-particles to pre-heat, and then continuously heat, a fluid in the bladder to enhance delivery of a chemotherapy substance such as Mitomycin-C (MMC), all while the fluid volume in the bladder is constantly changing. This approach is viable and does leave some engineering headroom in terms of modification of field strength and delivered nano-particle concentration. During this process, a given nano-particle concentration of 100 mg/ml was established in the bladder and that was sufficient to remain heat-able after a complete therapy session of 90 minutes, during which substantial fluid dilution is occurring due to the generation of urine by the kidneys. This result agrees in substance with laboratory tests using bladder "phantoms, comprised of a 'bladder' and 'kidneys'", which dilutes the nano-particle heating solution at a rate similar to a human body.

Assumptions:
  Start Concentration: 100 mg/ml of $Fe_3O_4$
  Start Volume: 20 ml, of $Fe_3O_4$
  Mitomycin-C: 40 ml (at desired concentration)
  Add MMC time is: after 15 minutes of pre-heat time
  Pre-Heat time: 15 minutes
  Treatment time: 60 minutes
  Cool-down time: 15 minutes
  Frequency 50,000 Hz
  Field Strength: varies from 2,000 to 5,000 A/m
  Particle Composition: magnetite 1, $Fe_3O_4$
  Particle Size: 18 nm plus 2 nm coating, hydrodynamic volume at 22 nm
  Viscosity: assumed bladder fluids approximates water
  Bladder Start Volume: 0 ml
  Bladder Fill Rate: 40 ml per hour from kidneys Max Bladder Capacity: 300 ml (can be upwards of 350 ml)

Urge to Urinate Point: 25% of bladder capacity or 75 ml

Heat loss rate of Bladder: 0.02° C. per sec, nominal

The nominal bladder heat loss rate, per study, is 0.01° C. to 0.02° C. per second and the max heat loss rate is 0.05° C. per second (muscle is −0.03° C./sec; kidney is −0.365° C./sec; spleen is −0.131° C./sec; liver is −0.124° C./sec).

Protocol

The protocol executed by the Body Cavity Cancer Treatment System involves inserting 20 ml of a nano-particle magnetite solution, having a concentration of 100 mg/ml; this is 2,000 mg of iron inserted into the bladder cavity as a fluid suspension. The Foley catheter (or other catheter) has at least one or more temperature sensing probes inside the bladder cavity. These temperature probes are fiber optic based to avoid interaction with the applied magnetic fields. Alternatively, or in concert with, the temperature can be measured via an external non-invasive process using, for example, an ultrasonic scan where the ultrasonic wave velocity changes as a function of tissue or fluid temperature. The temperature sensing data is fed to the computer 403 which operates the coil system 401, 402, where the computer 403 signals the amplifier 404 when to increase the current thru the coils 401, 402 to thereby increase the temperature of the fluid in the bladder which contains nano-particles by increasing the magnetic field strength.

A $Fe_3O_4$ Magnetite solution is then added to the bladder via a Foley catheter and the bladder is pre-heated for 15 minutes with 1.8° C. of rise every 5 minutes. This is an exemplary rate of heating and it can be faster or slower depending on the particle concentration and field strength. The bladder and nano-particle solution in the bladder are now nominally at 42° C.-43° C. The MMC can be pre-heated to 42° C. prior to adding it to the bladder via a Foley catheter. Then, 40 ml of MMC at its stated concentration is added to the bladder. A stasis temperature of 5° C. above body ambient is maintained for 60 minutes; this stasis temperature is nominally 42° C.-43° C.

During the entire procedure, the kidneys fill the bladder with urine at rate of 40 ml per hour for patients with a no-fluids diet. Then, the protocol of the Body Cavity Cancer Treatment System cools down the fluid and bladder to the body ambient temperature of 37° C.; this is after one hour with MMC on board with applied heat. The protocol is to cool down the fluid and body over 15 minutes versus hard shut down from 42° C.-43° C. to 37° C. The MMC is retained on board until a predetermined length of chemotherapy treatment have evolved; one hour with heat applied, the second hour without heat.

Graphical Illustration of the Operation of the Protocol

Figure 8:
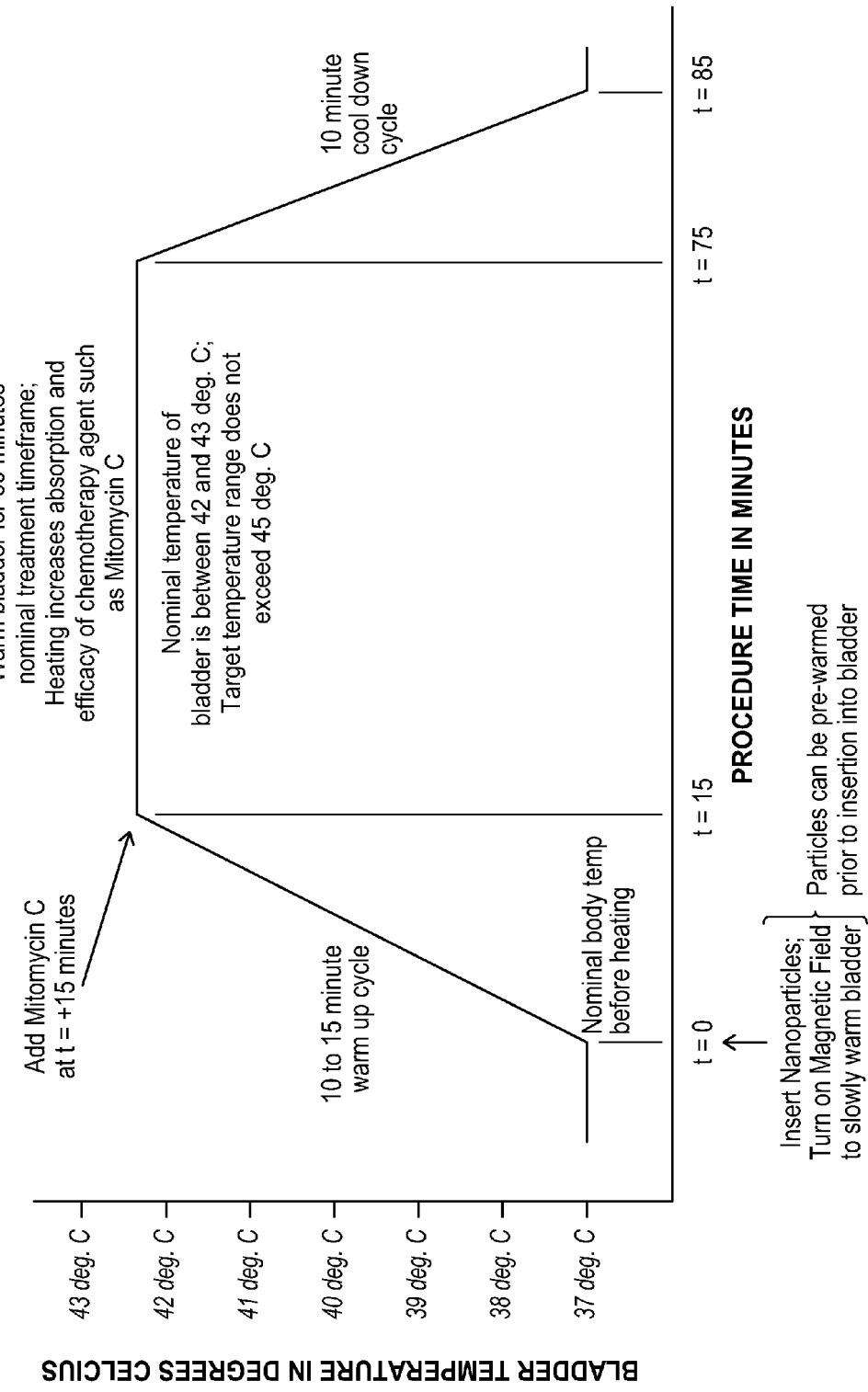
FIG. 8 illustrates in graphical form a first bladder cancer treatment protocol.
Figure 9:
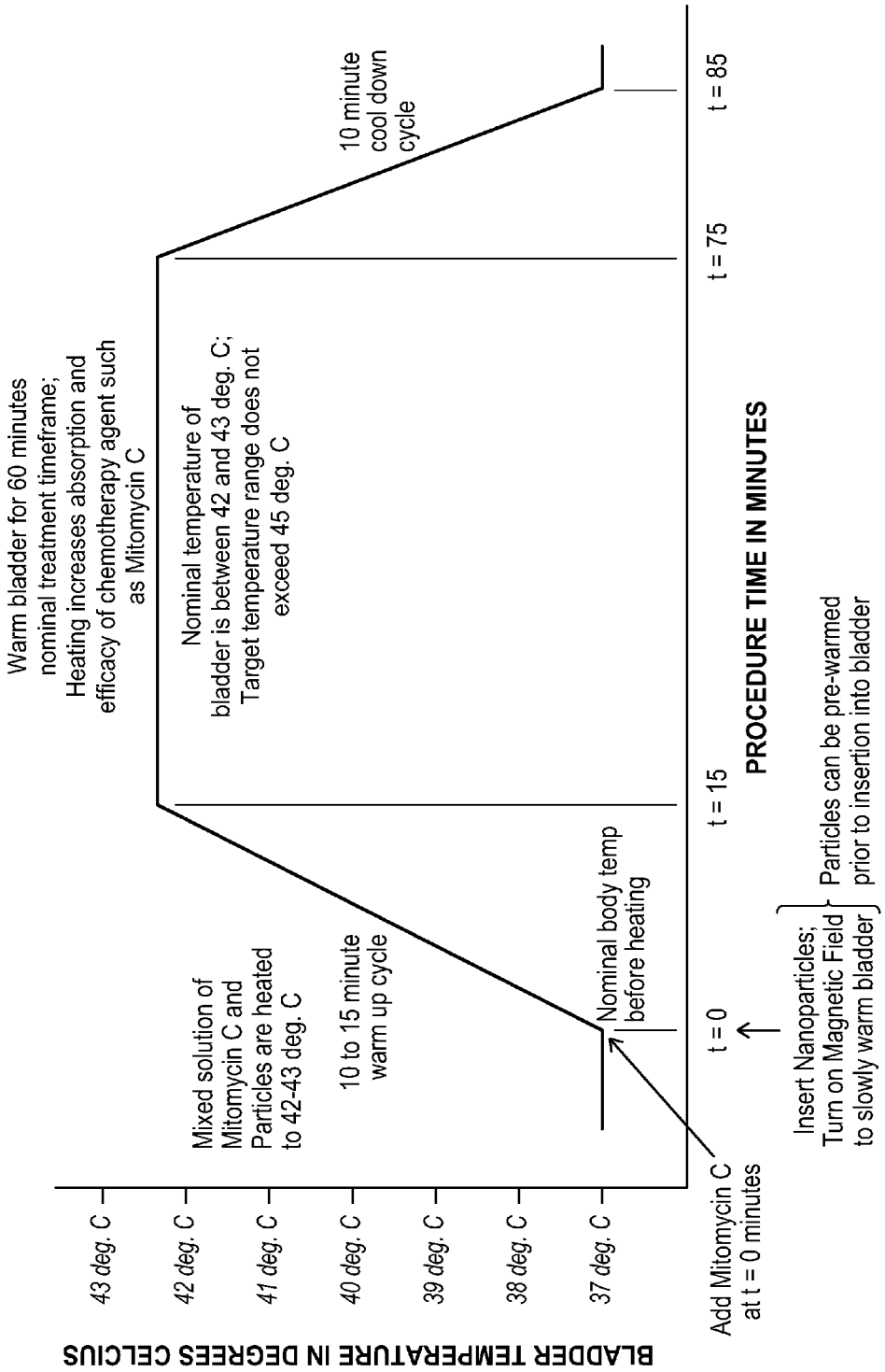
FIG. 9 illustrates in graphical form a second bladder cancer treatment protocol.

FIG. 8 shows an implementation of the protocol which is described above, where the bladder is first heated over a 15 minute timeframe to 42° C. to 43° C. using nano-particles and a magnetic field. At the t=15 minute mark, a chemotherapy drug, such as Mitomycin-C (MMC), can be pre heated and added to the bladder via a Foley catheter assembly. MMC is the preferred chemotherapy agent but other agents can also be used. FIG. 9 shows a protocol where the Mitomycin C (MMC) is preheated immediately and added to the bladder along with the nano-particles. The bladder is heated to a nominal 42° C.-43° C. over a 15 minute timeframe.

In either of these protocols, the treatment time frame is sixty minutes. There is a 10-15 minute temperature ramp from the body ambient temperature of 37° C. to the treatment temperature of 42° C.-43° C., where that treatment temp of 42° C.-43° C. is maintained for a 60 minute timeframe. After 60 minutes, there is a 10-15 minute cool down ramp.

The patient is generally advised to retain the chemotherapy agent inside their bladder for another 60 minutes without the addition of heat. At the end of that time frame, the patient then voids their bladder to remove the remaining chemotherapy agent and all or nearly all of the nano-particle solution. This procedure can be repeated as needed, as directed by existing or even new, modified overall protocols for bladder cancer.

Data

Figure 11:
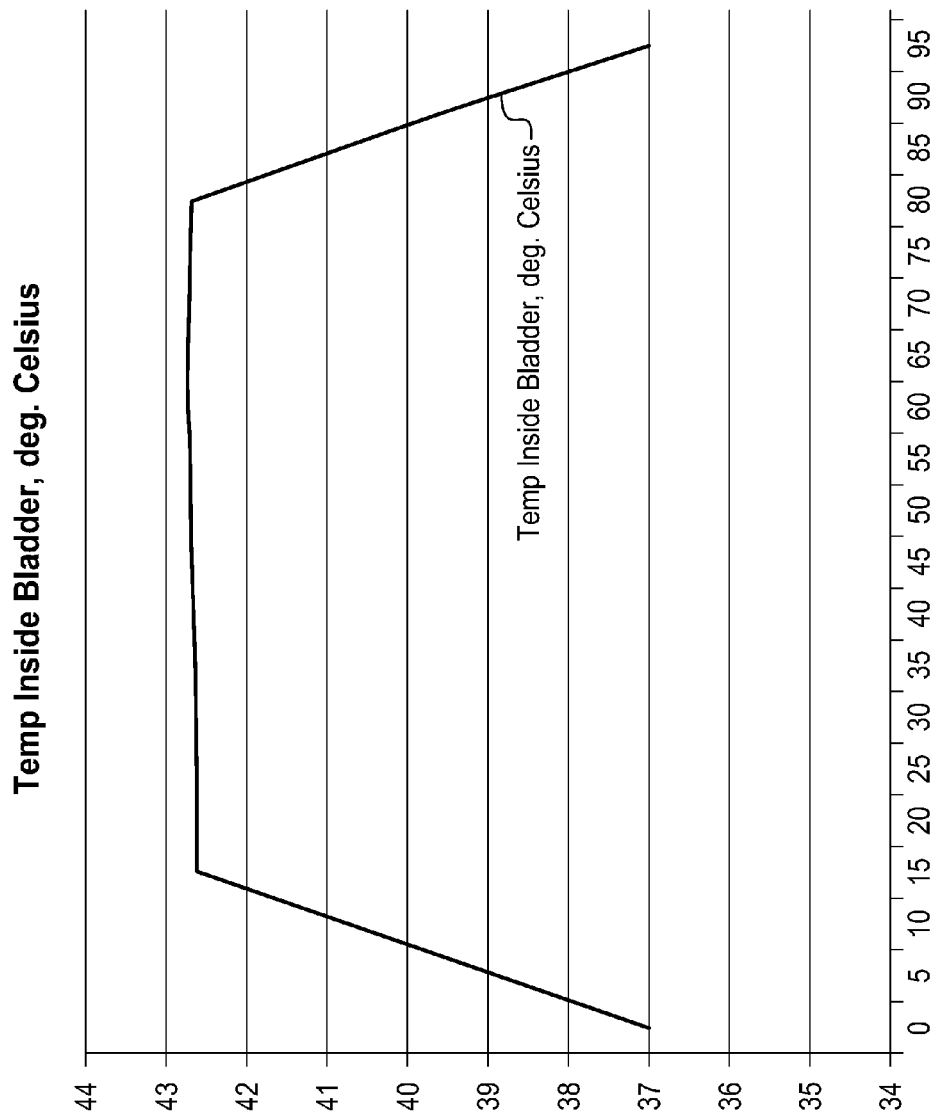
FIG. 11 illustrates in graphical form a plot of the measurement of the typical temperature inside the bladder, in degrees Celsius, vs time during the treatment protocol.

FIGS. 11-15 show, in graphical form, the estimated performance of the heating system as the particle concentration is diluted and the field rate is adjusted to maintain a stasis temperature of about 5° C. rise above body ambient. FIG. 11 illustrates in graphical form a plot of the measurement of the typical temperature inside the bladder, in degrees Celsius, vs. time during the treatment protocol. The present protocol pre-heats the bladder for 15 minutes at the determined rise rate of 1.8° C. per every 5 minutes to reach stasis temperature of 42.5° C. at 15 minutes. At this point in time, the bladder is at 42° C.-43° C. as shown in this graph. The Y or vertical axis is degrees Celsius and the X or horizontal axis is minutes elapsed. At 15 minutes into the procedure, 40 ml of MMC (Mitomycin C) is added (which is pre-heated to 42° C.); and to maintain temperature, the field strength is increased to 2,500 A/m. The nano-particle concentration is further diluted by the kidneys producing urine at 40 ml per hour. Therefore, the field strength must be increased at the given rate, moving from 2,500 A/m to just over 3,000 A/m. The maximum field strength is a little greater than 3,000 A/m. This is 0.3 times the nominal one Brezovich limit to avoid eddy currents inadvertently heating the tissue. The Brezovich limit is the frequency times the field strength divided by a constant of $4.85E^8$. At 0.3 times the Brezovich limit, this treatment protocol absolutely does not cause any inadvertent tissue heating from eddy currents. Only the particles heat via magnetic Brownian excitation, and then via fluid convection, the bladder tissue heats; no other tissue inadvertently heats, such as occurs with existing prior art treatment methods.

In Brownian excitation, the nano-particles actually physically rotate, based on the frequency of illumination and the viscosity of the fluid containing the particles. For this particular particle size, frequency and fluid viscosity, there is a very small contribution from Neel heating, but since it is de minimus, it is not considered. Ned heating is when the magnetic domains align and un-align; this process causes heat. In Ned heating, the particles do not physically move.

Figure 12:
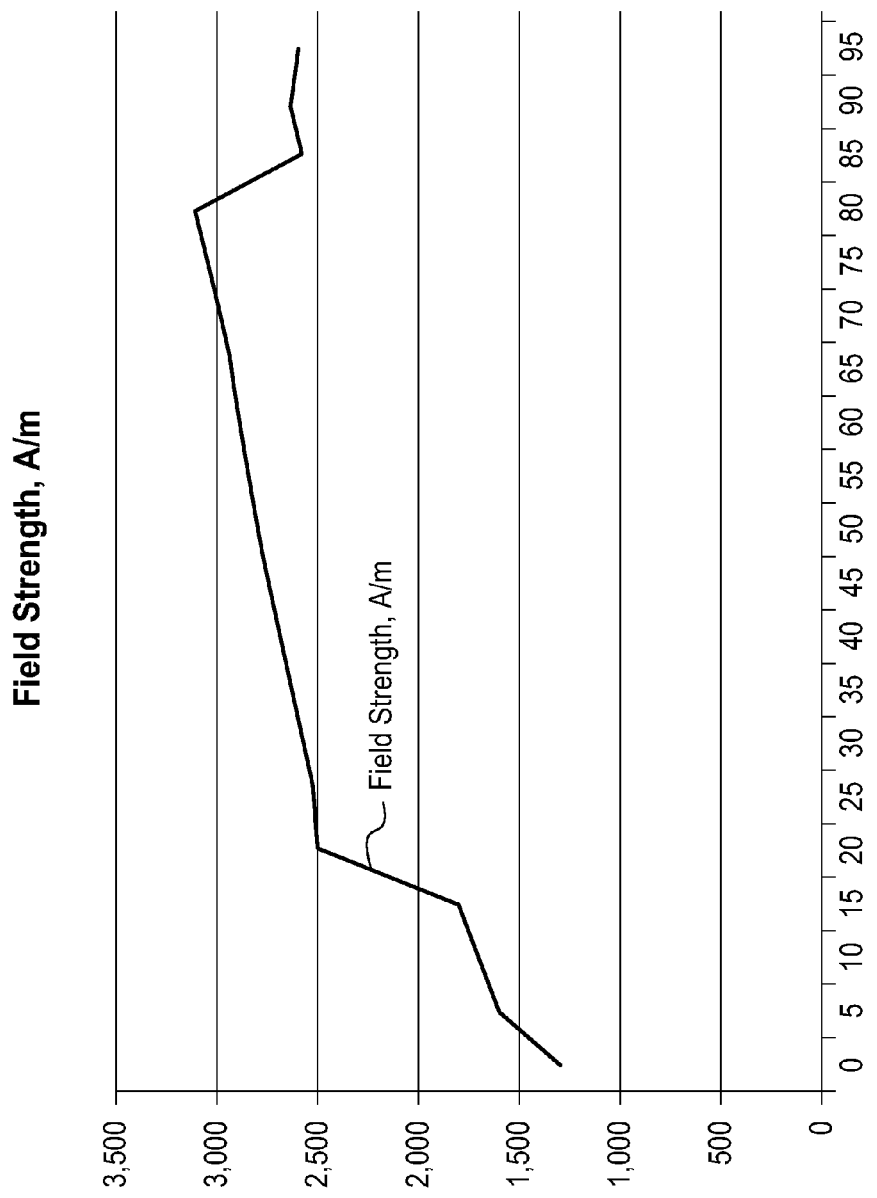
FIG. 12 illustrates in graphical form a plot of the measurement of the typical field strength in Amps/meter vs time during the treatment protocol.
Figure 13:
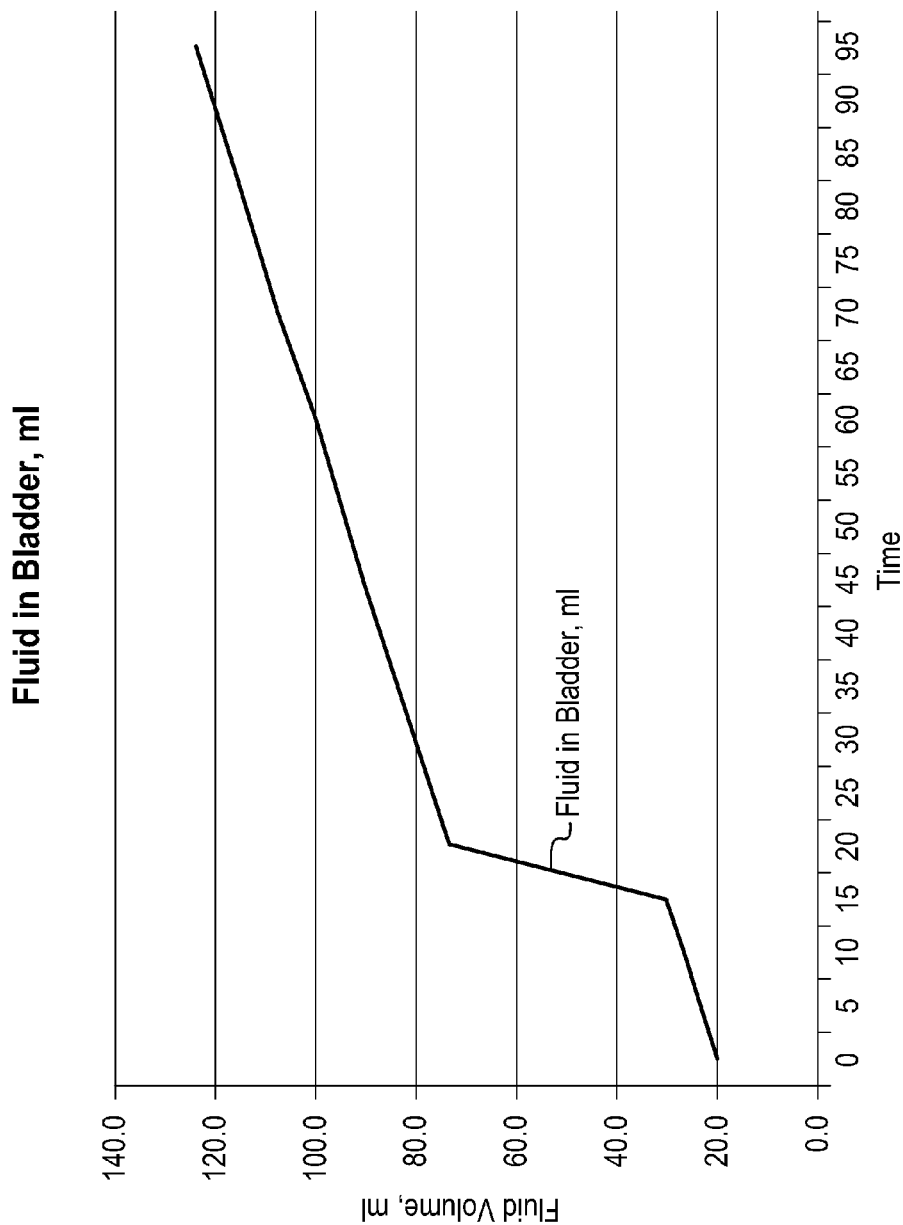
FIG. 13 illustrates in graphical form a plot of the measurement of the typical bladder fluid volume in milliliters vs time during the treatment protocol.

FIG. 12 illustrates in graphical form a plot of the measurement of the typical field strength in Amps/meter vs. time during the treatment protocol (vertical or Y axis) with the horizontal or X axis as time in minutes. FIG. 13 illustrates in graphical form a measurement of the typical bladder fluid volume in milliliters during the treatment protocol. Initially, 20 ml of MMC are added which is the 100 mg/ml concentration of $Fe_3O_4$. At 15 minutes in, 40 ml of MMC is added. Throughout the process, from time equal to zero, the kidneys are adding 40 ml of urine per hour. At 25% of full bladder volume of, for example, 300 ml (or 75 ml's), the patient will begin to feel an urge to vacate the bladder. At 120 m of volume, the urge to void the bladder has grown but should be "patient tolerable" based on studies and research. The "Fluid in Bladder" plot shows the level of fluid in the bladder or time; the Y axis is in milliliters and the X axis is in minutes of time. The particle concentration falls to below 20 mg/ml near the end of the treatment cycle. That is because the procedure started with a particle concentration of 100 mg/ml and dilution from the added Mitomycin C and the contribution from the kidneys, causes the end resulting nano-particle concentration to be just below 20 mg per milliliter.

Since the system is not near the design maximum of 5,000 A/m, there is sufficient field strength headroom to heat even lower concentrations of nano-particles. The minimum concentration of nano-particles is on the order of 5 mg/ml, any concentrations below that level are difficult to heat. Other procedures that add greater amounts of fluid might need to start with higher nano-particle concentrations. It is believed that for magnetite $Fe_3O_4$ in a water based solution that the maximum concentration is in the 250-300 mg/ml range before it begins to become too thick and viscous to be practical to use.

Figure 14:
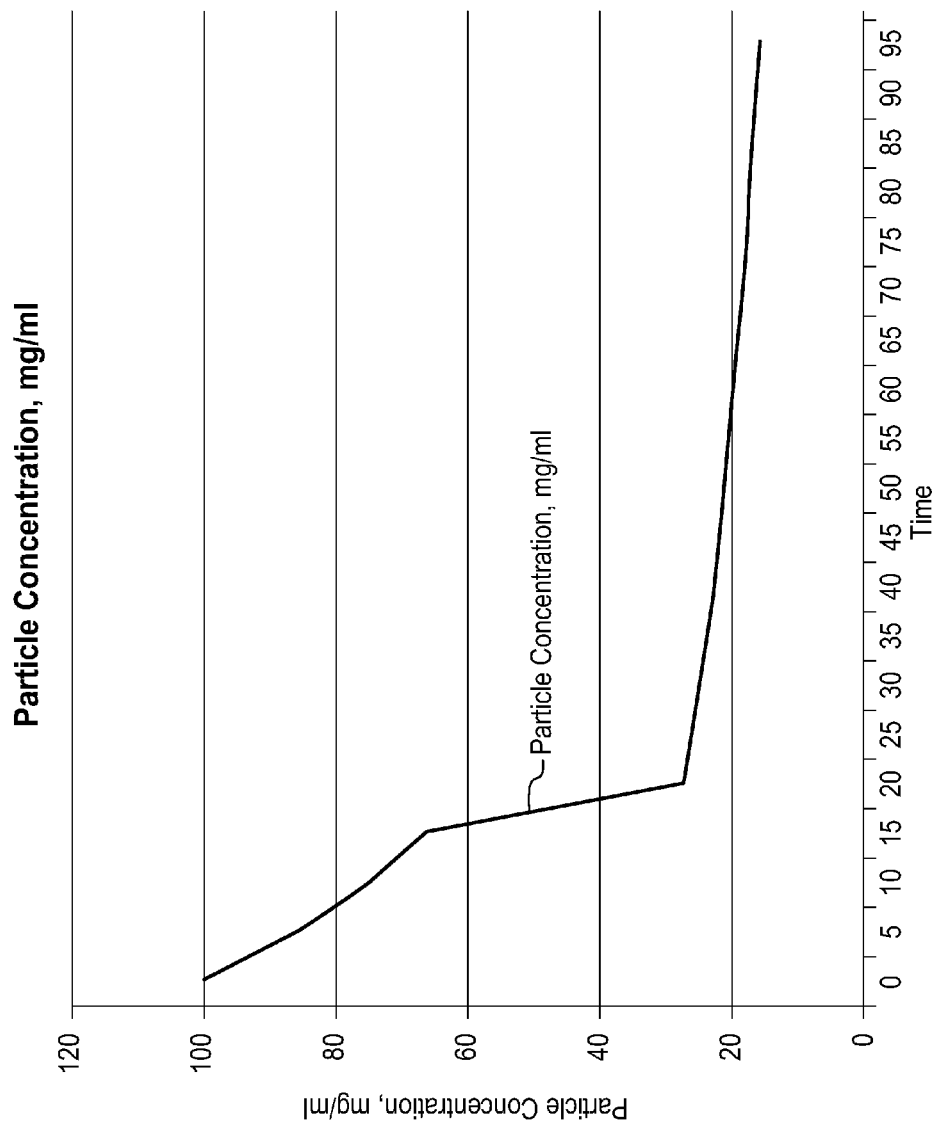
FIG. 14 illustrates in graphical form a plot of the measurement of the typical particle concentration in milligrams/milliliter vs time during the treatment protocol.
Figure 15:
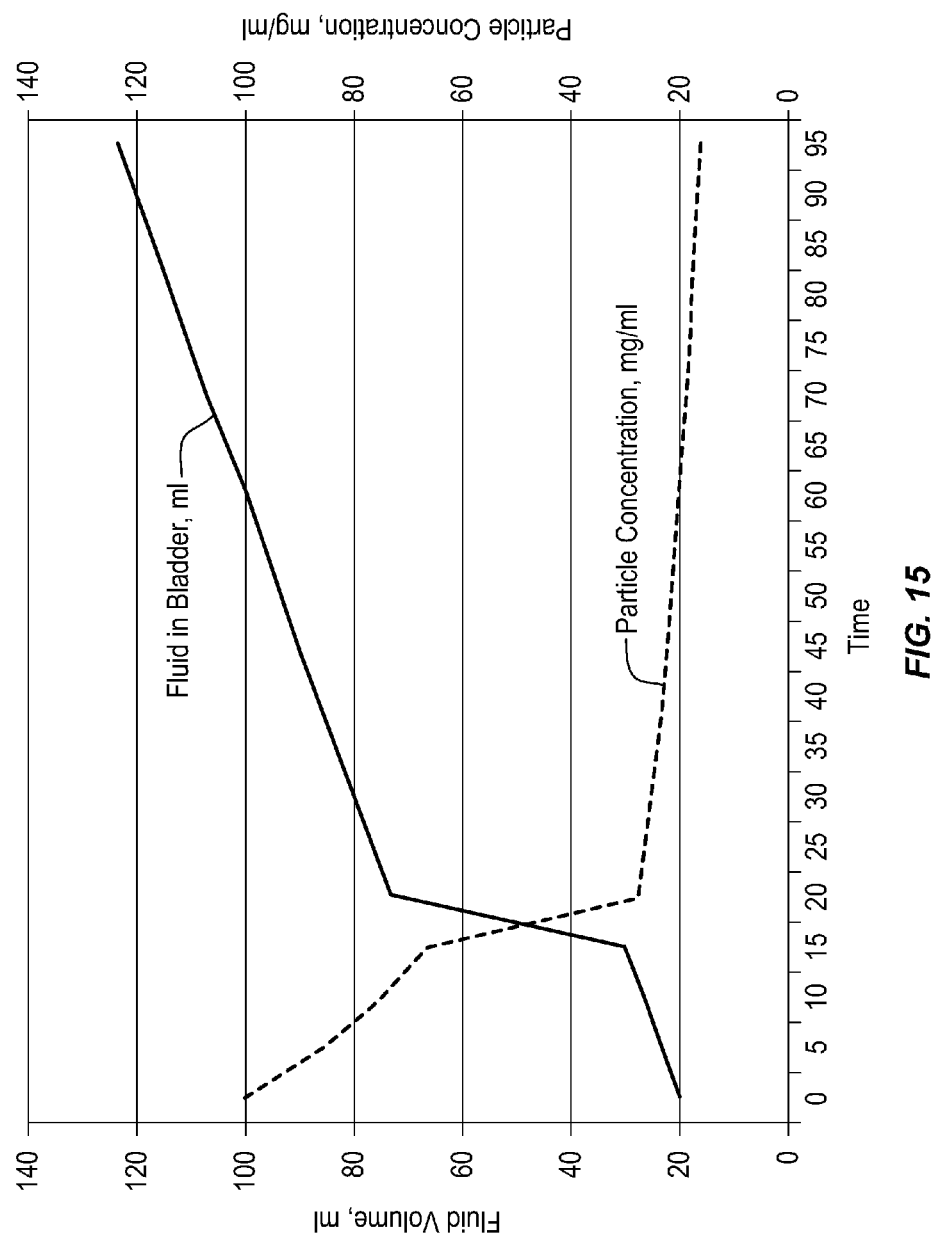
FIG. 15 illustrates in graphical form a plot of the measurement of the typical particle concentration in milligrams/milliliter during the treatment protocol as overlaid on the typical bladder fluid volume in milliliters vs time during the treatment protocol.

FIG. 14 illustrates in graphical form a plot of the measurement of the typical particle concentration in milligrams/milliliter vs. time during the treatment protocol. It starts at 100 mg/ml, and then thru various dilutive steps noted above, it ends up in the 19 mg/ml range. At 15 minutes into the procedure, the Mitomycin C is added (40 ml's) and then kidney based dilution at a flow rate of a patient who has been on a no liquids diet. FIG. 15 illustrates in graphical form a plot of the measurement of the typical particle concentration in milligrams/milliliter vs. time during the treatment protocol as overlaid on a plot of the typical bladder fluid volume in milliliters vs. time during the treatment protocol. Blue shows the particle concentration in mg/ml versus time in minutes and overlaid with it is the fluid volume in the bladder in milliliters versus time in minutes.

The Actium Condition

The Actium Condition is a state where nano-particle heating is optimized while the probability of tissue heating via unintended eddy currents is minimized. Brezovich, when he created the condition of f*H with respect to a constant of $4.85E^8$, did not do so in the context of nano-particle heating. He was only concerned with the unintended creation of eddy currents which heats tissue not having nano-particles, which in reality is measured to be $f*H^2$. When the context of nano-particle heating is added to a fixed value of $f*H^2$, an optimal operating point with respect to frequency is realized. Since the particle heating, prior to particle magnetic saturation, is a function of the field strength squared, it is desirable to maximize the field strength versus frequency. This means lower frequencies with a given field strength yields significantly higher rates of nano-particle heating without creating unintended eddy currents which heats tissue not nano-particles.

Since the frequency needs to be at least above 10 KHz to avoid nerve/muscle excitation, a safety zone is created by heating the nano-particles at 40 KHz, well above the frequencies where nerves are excited. Since f*H is the second constraint, the field strength for one Brezovich limit is 9,700 A/m. Since this study shows a maximum field strength of around 3,100 A/m, we are now operating a level of 0.3 Brezovich limits—thus, we have optimized the heating of the particles while minimizing the possibility of unintended eddy currents.

Summary

This sample protocol provides a method and procedure to effectively treat bladder cancer using Actium BioSystems based technology. At every step of the process, there is significant "headroom" to adjust various parameters to match or meet the unique needs of a given patient population as well as a treating physician's desired protocol.

Bladder Heat Loss Analysis

Actium scientists have conducted an extensive analysis of the bladder heat loss, to ensure that on the field strength side of things, that there is sufficient heating capacity to overcome the body's natural ability to remove heat via circulating blood flow. The Bio Heat Equation developed by Pennes (1948) is the most widely used thermal model for biological tissue $$\rho C \frac{\partial T}{\partial t} = \nabla \cdot (K \nabla T) - \rho_b C_b w(T - T_b) + Q_m + Q_s$$

$\rho$, C, K, and T are the density, specific heat, thermal conductivity, and temperature of the tissue, respectively.

$\rho_b$, $C_b$, $T_b$, w are the density, specific heat, temperature, and volumetric flow rate of blood.

$Q_m$ is the metabolic heat production and $Q_s$ is the heating potential from an external source (such as electromagnetic illumination or magnetic induction).

Blood flow or perfusion is the most significant factor impacting the heat dissipation rate of tissue. To solely calculate heat dissipation due to blood perfusion, the following assumptions need to be made:

No temperature gradient in the tissue
No metabolic heat sources
No external heat sources These assumptions lead to the following equation for heat dissipation:

$$\frac{\Delta T}{\Delta t} = \frac{-\rho_b C_b w(T - T_b)}{C}$$

The table below shows the temperature loss rate for various tissue types using the equation above at T=43° C. ($\rho_b$=1058 [kg/m³], $C_b$=3840, [J/(kg ° C.)] $T_b$=37° C.). The data for the volumetric blood flow rates is from various animal and human studies. The range seen in the blood flow rates is due to a number of factors such as temperature variations and location of measurement (e.g., inner or outer periphery of tumor).

Generally, it is well accepted that blood perfusion in healthy tissue is greater than malignant tissue. This is especially true when the temperature of the malignant tissue is raised by an external source, such as in hyperthermia treatments. The blood flow rate in normal tissue can increase by a factor of ~8 when its temperature increases. However, measurements have shown that in malignant tissue the increase in the blood flow rate is almost negligible when its temperature increases. Therefore malignant tissue is much more susceptible to heat damage.

TABLE 1

| Tissue Properties | | |
|---|---|---|
| Tissue Type | $C_P$ [J/(kg ° C.)] | ρ [kg/m³] |
| Blood | 3840 | 1058 |
| Muscle | 3720 | — |
| Tumor | 3049 | — |
| Fat | 2279 | — |

TABLE 1-continued

Tissue Properties

| Tissue Type | $C_P$ [J/(kg·°C.)] | ρ [kg/m³] |
|---|---|---|
| Kidney | 3890 | — |
| Liver | 3600 | — |
| Spleen | 3720 | — |

TABLE 2

Heat loss rates for different tissue types

| Tissue Type | $T_{w\text{-}data}$ [°C.] | w [m³/kg/s] | ΔT/Δt [°C./s] |
|---|---|---|---|
| Muscle | — | 4.05 × 10⁻⁶ | −0.027 |
| Muscle | 43 | 1.3 × 10⁻⁶ | −0.009 |
| Muscle | 43 | 4.74 × 10⁻⁶ | −0.031 |
| Tumor | — | 4.5 × 10⁻⁷ | −0.004 |
| Tumor | 43 | 2.34 × 10⁻⁶ | −0.019 |
| Tumor | 43 | 7.8 × 10⁻⁷ | −0.006 |
| Tumor | 43 | 1.3 × 10⁻⁷ | −0.001 |
| Fat | — | 3.07 × 10⁻⁷ | −0.003 |
| Kidney | — | 5.83 × 10⁻⁵ | −0.365 |
| Liver | — | 1.83 × 10⁻⁵ | −0.124 |
| Spleen | — | 2 × 10⁻⁵ | −0.131 |

Zero Temperature Gradient

End of treatment temperature in the bladder is ~42° C. This ~5° C. temperature gradient has a moderate impact on the temperature dissipation of bladder. The impact of this assumption depends on the time of illumination with no metabolic heat source. Body temperature is naturally at 37° C. Since we are not cooling, neglecting the metabolic heat source is reasonable.

The next section considers the blood vessels ability to remove heat from regions that are being heated. The nanoparticles, heated via a magnetic field, must have sufficient heating headroom to overcome any natural heat removal mechanisms of the body. The primary mechanism for heat removal is via blood vessels, when dilated, enables greater volumes of blood flow, hence heat removal. This dilation process enhances the ability of the vasculature to remove heat. Each organ type, skin-liver-bladder, for instance, has different levels of heat removal capability. Since we are interested in the bladder at the moment, the Pennes Bio-Heat equation was used to calculate the bladder's ability to remove heat.

Blood flow rates vary for different tissue types

Kidney and liver perfusion rates are much higher than fatty tissues

Blood flow rates are temperature dependent

Tissue is cooled by increased blood flow, which carries the heat away from thermally hot regions of the body. This process works extraordinarily well provided that the thermal load is not systemic, where at that point the body is in overload and things like heat shock or heat stroke can occur. The Actium process takes into consideration the thermal cooling characteristics of a given region of the human body.

Figure 10:
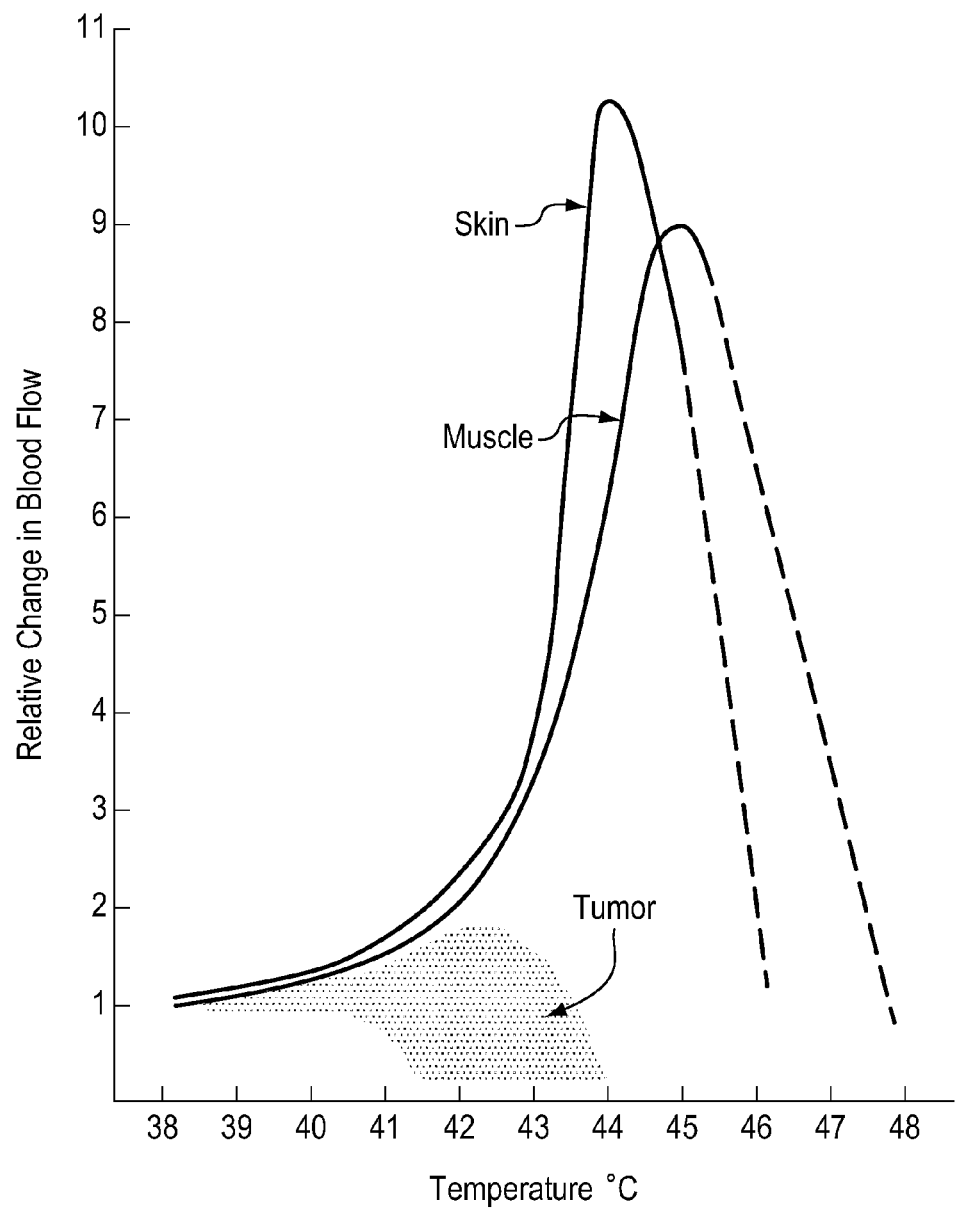
FIG. 10 illustrates in graphical form a plot of the relative change in blood flow in skin, muscle and a tumor as plotted against temperature.

In general, tumors have very poor blood perfusion, meaning tumors are unable to remove heat (see the dotted region in the "Song" graph of FIG. 10 above). Muscle has upwards of 6 times the ability to remove heat relative to a tumor. And, as the temperature is increased to 44° C., tumors cannot keep up with the thermal load.

Bladder Blood Flow

In general, the bladder is not very well perfused relative to other body organs. This means that the bladder does not remove heat very efficiently. This is advantageous for the Actium treatment protocol—magnetic field strengths can be kept to low relative levels (no tissue heating eddy currents), the concentration of magnetic particles can be kept to reasonable values (this keeps the cost of the material down for treatments), the level of amplification can be lower, the component ratings can be lower—all of these things help reduce the cost of the machine (device).

Figure 16:
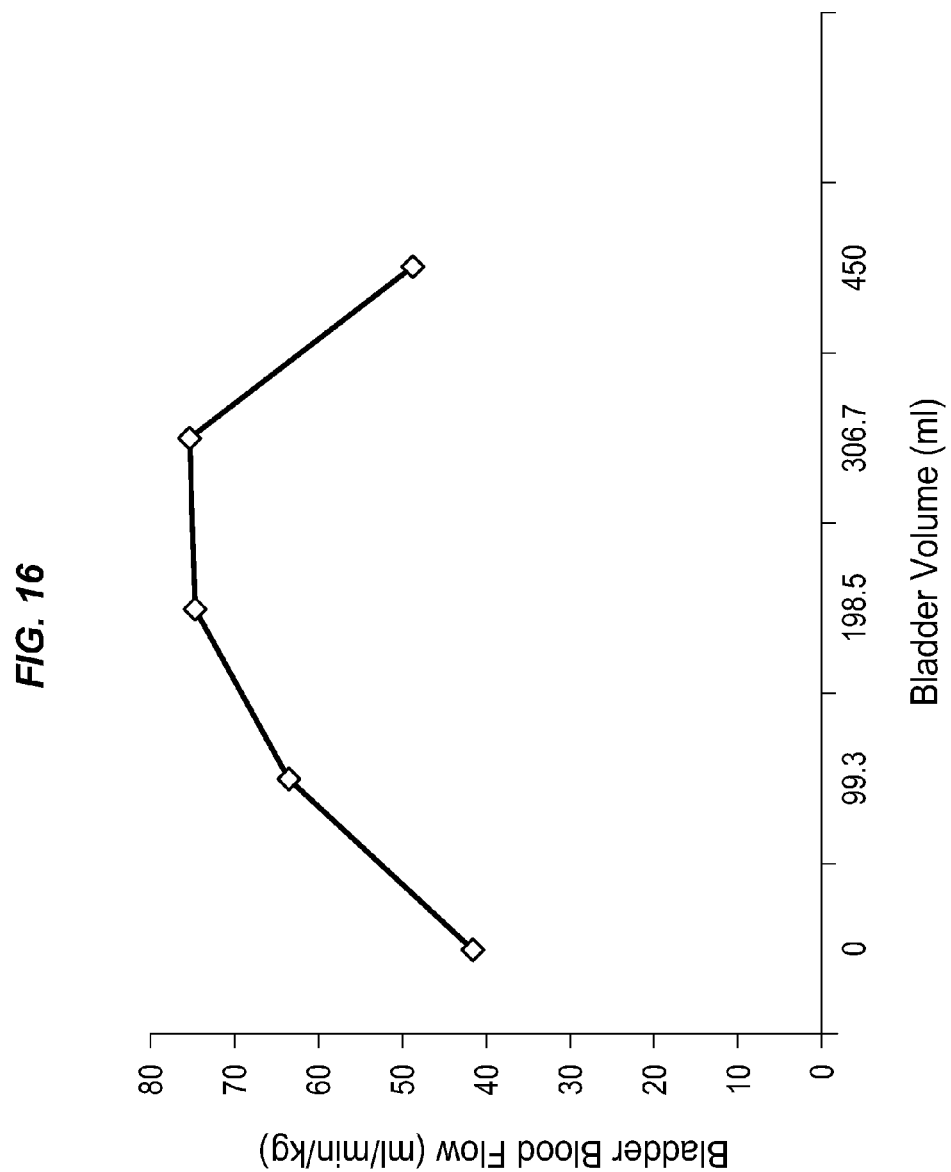
FIG. 16 illustrates in graphical form a plot of bladder blood flow vs bladder volume.

Bladder blood flow rate: ~0.06% of cardiac output and the bladder blood flow rate is a function of bladder volume where FIG. 16 illustrates in graphical form a plot of bladder blood flow vs. bladder volume. The far right side of the plot shows the blood flow rate falling off as the bladder reaches a volume of around 300 milliliters; this is because the blood vessels get compressed.

The reasons for these different blood flow rates follow:
  Empty/Collapsed Bladder (Left Side of Plot)
    bladder microvasculature is extremely tortuous and tightly coiled
    this means the blood vessels have high resistance and low blood flow
  Non-Empty Bladder (Left/Middle Region of Plot)
    bladder microvasculature stretches and expands
    blood vessels have lower resistance and higher blood flow
  Full Bladder (Far Right Side of Plot)
    bladder microvasculature is compressed
    this causes a decrease in blood flow Studies have shown that when "muscle" in general reaches 42° C. relative to body ambient of 37° C., the relative blood flow rate increase by a factor of 2. Since virtually all of the blood flow of the bladder is in the detrusor muscle, the maximum thermal dissipation rate of the bladder is 0.05° C. per second at 42° C. The average bladder thermal dissipation rate, with 40-120 milliliters of fluid in the bladder, is 0.008 to 0.012° C. per second. Therefore, to be conservative, and as indicated in the previous modeling of the complete treatment protocol, the model used 0.02° C. per second as the bladder's nominal thermal heat loss rate.

The Bladder Heating Model with Eddy Currents

Separately, full body models have been completed using a second simulation step where it uses biological heat removal models such as the Pennes Bio Heat Equations to predict what the body's heating is from the eddy currents. The Thermal model yielded a complete body temperature analysis which showed that for the 2,500-3,000 A/m illumination protocol previously shown, for the bladder example, the average tissue temperature from eddy currents is in the neighborhood of 0.4° Celsius . . . virtually indistinguishable. The peak temperature from eddy currents was seen to be around 0.9° C. for a very small tissue region. In addition to keeping the f*H product low, and keeping the magnetic field strength low (H), there are many other methods in the toolbox to manage eddy currents and unintended tissue heating.

It is important to note that the methods discussed next, to lower the probability and level of unintended tissue heating, are not necessary or required since the examples provided herein heat just fine. They are merely ideas and concepts created to use should this ever become an issue. Methods to manage unintended tissue heating:
  Use Mu Metal to shield certain areas of the body
  Use active magnetic field cancellation (discussed next)
  Use higher magnetic nano-particle concentrations—the bladder example used 100 mg/ml of 20 nm sized Fe3O4. It is believed that starting nano-particle fluid concentrations can go upwards of 300 mg/ml; this means that the field strength needed, hence reduced eddy current levels, and is improved.

Use the lowest fluid levels possible for both the nano-particles as well as the applied chemotherapy agent. Lower dilution means higher heating with lower magnetic field strengths.

Lower the excitation frequency slightly to 30-40 KHz. A lower frequency means a higher field strength can be used which yields faster nano-particle heating in contrast to any created eddy currents.

Optimize the nano-particle size distribution only have nano-particles which are at the desired size of nominally 20 nanometers in diameter (hydrodynamic size).

Increase the magnetization of the nano-particles. By increasing the magnetization of the nano-particles, the nano-particles heat at a significantly greater rate for a given applied magnetic field.

Apply a DC magnetic field in the areas where zero AC magnetic field is needed; a DC magnetic field tends to counter or reduce the magnitude of the AC magnetic field.

Use a grounding strip on the body to short our any surface currents on the body.

Change the position of the Helmholtz coils (other) to a position which minimizes the formation of eddy currents.

Use a carbon loaded blanket on the body parts not being illuminated with the magnetic field. Eddy currents can exist beyond the area where the B, H field exists, and so these areas would be "absorbed".

Blocking or Shielding Vital Organs

When the nano-particles are delivered via an IV or Intravenous tubes, the nano-particles that are not taken up by the cancer are eventually removed by the body's filtering organs. This is not an issue for the "cavity" method such as for the bladder. Certain vital organs which are responsible for filtering out foreign objects from the body include the kidneys, the spleen and the liver. These vital organs remove nano-particles from the body which are not taken up in a cancerous region. It is conceivably possible that these organs could have nano-particles residing in them during a magnetic illumination protocol for cancer, where nano-particles purposefully reside in the cancerous region. It is desirous to block or shield these vital organs from illumination of the magnetic field to a level at least one order of magnitude, as an initial design objective. One order of magnitude in field reduction yields a 50 times reduction in heating rate (for the assumptions listed below).

Given that heating is a function of the magnetic field squared, a ten times reduction of the magnetic field results in a heating rate reduction of 50 times (Brownian heating, viscosity is 2× water, 50 KHz, 50 mg/ml, 20 nm diameter particles). The heating rate at 8,600 A/m is 0.4073° K/sec while the heating rate at 860 A/m is 0.0082° K/sec for a heating ratio of around 50 times (again, both are for 20 nm diameter particles). The field strength of 8,600 A/m is only used during the 2-3 minutes heating phase from 37° C. to 42° C.

In practice, when at 42° C., the rate of heat input needs to only match the rate of heat loss to stay at 42° C. The average tumor heat loss rate is 0.0075 deg/sec. However healthy tissue has an average heat loss rate significantly higher due to the more organized and more efficiently operating blood perfusion in healthy tissue. In a person that has cancer, the liver/kidneys/spleen could be taxed and working over-time to try and rid the body of cancerous cells, but the vital organs should have better perfusion and should be able to remove heat at a much higher rate than cancer.

During the steady state phases of maintaining a continuous temperature of 42° C., the field strength at 50 mg/ml is 2,722 A/m. Our target field strength for the vital organs is 272 A/m or less (one tenth or less the incident field strength in the cancerous region). At 272 A/m, the field strength is 0.0003427 Tesla (for the spreadsheet input); the particle concentration is assumed to be 50 mg/ml in the vital organs. Putting this Tesla value into computer models for Brownian heating, we get plus 0.0008 deg K/sec heat added into the vital organ containing nano-particles at 50 mg·ml.

Even fat, with its very poor blood perfusion, has a heat loss rate of minus 0.003 deg/sec; this means that even fat would easily remove this very low added heat with zero net temperature increase. The vital organs, with their enhanced perfusion, even if impaired in a cancer patient, would easily remove this level of added heat (plus 0.0008° K/sec). Thus, a ten times reduction in field strength for the vital organs seems to be a good starting point for the design goal of our blocking or shielding algorithms.

The heat loss rates for healthy" vital organs" is decidedly greater than that for other tissue types due to the large supply of blood perfusion. The Kidney is negative 0.365 deg per second, the Liver is negative 0.124 deg per second and the Spleen is negative 0.131 deg per second. These heat loss rates swamp the plus 0.0008 deg/sec heating rate after a ten times reduction in field strength is applied (50 mg/ml, 272 A/m or lower).

Thus, a ten times reduction in field strength in the volumetric region of vital organs is sufficient (ten times lower than the treatment field strength in the cancerous volumetric region). The natural heat loss rates of these organs further ensures that these organs, when they are removing nano-particles, in concert with a low level applied field, will not heat at all.

It is possible that 42° C. is not optimal, or is not optimal for a given person with a given cancer. Nothing herein limits these concepts to a fixed temperature of 42° C. The system can be adjusted to realize any new temperature, say 44° C. For example, some studies have indicated that 15 minutes at 44° C. is equivalent to 2 hours at 42° C. in terms of its biological benefit and effect.

At less than one Brezovich limit, the Body Cavity Cancer Treatment Apparatus causes virtually no unintended heating via eddy currents in tissue without particles. When compared to MRI maximum SAR limits (Specific Absorption Ratio), the Actium system is many orders of magnitude below the stated MRI heating maximums (MRI's use magnetic fields at higher frequencies). When running a full body model for a bladder cancer heating example at 3,000 A/m, the average temperature caused by an eddy current is plus 0.4° Celsius over body ambient—virtually zero. And, the fluid in the bladder is heated to a nominal 42° C. for a full hour or longer by using a magnetite nano-particle fluid in the bladder susceptible to heating by a magnetic field. It is important to protect organs that may have filtered out nano-particles IF the nano-particles are delivered via IV. Organs that may have taken up nano-particles include the: spleen, liver and kidneys. The first method is passive and uses a material that has a very high relative magnetic permeability (Ur of 80,000 to 100,000) to "block" the fields. This material would be used above and below the body in the region of the vital organs. The second method is "active" and involves the use of a smaller excited coil inside the larger 60 cm coil. By varying or adjusting both the magnitude and phase of the drive current of the smaller "blocking" coil, the fields can be "cancelled" in the region of the vital organs. Note that for either method; passive vs. active, energy is not "destroyed" meaning the magnetic fields are not "destroyed". Rather, the fields are re-directed or re-shaped away from the vital organs.

Field strengths sufficient to heat nano-particles at very low concentrations are easily achieved. The product of the excitation frequency and the field strength is sufficiently low to not cause unintended tissue heating while at the same time optimizing the heating of nano-particles in the Brownian magnetic region. Finally, the body's filtering organs, containing nano-particles, can be shielded so that they do not heat during a cancer treatment protocol. The tools available in the toolbox are versatile and many, there is nothing that can't solved.

The concept of using the body's natural cavities, or the creation of temporary cavities, enables very precise control of the nano-particles and the illumination process is very easily implemented. In addition, after the heating protocol is completed, the nano-particles are completely or nearly completely removed. This eliminates much of the issues and operating concerns if the nano-particles are delivered via IV.

Summary

The Body Cavity Cancer Treatment System achieves extremely uniform temperatures inside the tissue of the body cavity thereby realizing optimal efficacy in enhancing operation of the chemotherapy agent while avoiding harm or pain to the patient. This is accomplished by the inclusion of "target particles", such as nano-particles, into the body cavity along with the chemotherapy agent to enable the use of an externally generated energy field to cause heating of the chemotherapy agent and the surrounding tissue of the body cavity by the activation of the nano-particles. The proper selection of the applied energy field enables precise control of the heat generated by the movement of the nano-particles.

What is claimed:

1. A method for treating cancer which is sited in a cavity that is located in a body, comprising the steps of:
    inserting a fluid, infused with magnetic particles, at a concentration between 5 and 300 milligrams per milliliter, into the cavity;
    selecting characteristics of an alternating magnetic field which energizes the magnetic particles to produce thermal energy;
    generating the alternating magnetic field;
    exciting the magnetic particles inserted into the cavity with the alternating magnetic field having a field strength between 2,500 and 8,600 amperes per meter, to produce thermal energy to regulate the temperature of the fluid in the cavity;
    sensing the temperature within or near to the cavity;
    raising the temperature in the cavity to between 42 degrees Celsius and 44 degrees Celsius at a predetermined rate of rise of temperature;
    inserting a chemotherapy drug into the cavity to allow the drug and the magnetic particles to freely mix together; and
    maintaining the temperature of the fluid in the cavity at the predetermined target level for a predetermined time in response to the sensed temperature by adjusting the alternating magnetic field.

2. The method of treating cancer of claim 1 wherein the predetermined time is between 15 and 60 minutes.

3. The method of treating cancer of claim 1 further comprising the step of: infusing a chemotherapy drug into the cavity when the fluid containing the magnetic particles has reached a predetermined temperature.

4. The method of treating cancer of claim 1 further comprising the step of: applying radiotherapy to the cavity.

5. The method of treating cancer of claim 1 wherein the rate of rise of temperature is 0.4 degrees Kelvin per minute.

6. The method of treating cancer of claim 1 wherein the magnetic particles are maintained at a predetermined concentration range during the duration of excitation.

7. The method of treating cancer of claim 1 wherein the concentration of magnetic particles is between 20 and 100 milligrams per milliliter.

8. The method of treating cancer of claim 1 wherein the chemotherapy drug is selected from a group comprising Mitomycin-C and a PARP (Poly Adenosine DiPhosphate Ribose Polymerase) inhibitor.

9. The method of treating cancer of claim 1 wherein the temperature is sensed by a thermocouple or optical fiber temperature sensor.

10. The method of treating cancer of claim 9 wherein the temperature is sensed in at least two locations.

11. The method of treating cancer of claim 1 wherein the frequency of the alternating magnetic field is between 40 and 100 kilohertz.

12. An apparatus for treating cancer which is sited in a cavity that is located in a patient's body, the apparatus comprising:
    an alternating magnetic field generator;
    an alternating magnetic field generator controller in communication with the alternating magnetic field generator; and
    a temperature sensor in communication with the alternating magnetic field generator controller,
    wherein the alternating magnetic field generator generates an alternating magnetic field having a field strength of between 2500 and 8600 amperes per meter, that raises the temperature of magnetic particles in a fluid in the cavity to between 42 degrees Celsius and 44 degrees Celsius at a predetermined rate of rise of temperature, and
    wherein the alternating magnetic field generator controller maintains the temperature of the fluid in the cavity at between 42 degrees Celsius and 44 degrees Celsius for a predetermined time in response to temperature measurements from the temperature sensor by adjusting the alternating magnetic field, and
    wherein the magnetic particles in the fluid are at a concentration between 5 and 300 milligrams per milliliter.

13. The apparatus for treating cancer of claim 12 wherein the rate of rise of temperature is at least 0.4 degrees Kelvin per minute.

* * * * *